United States Patent [19]

Vogelbacher et al.

[11] Patent Number: 5,185,027

[45] Date of Patent: Feb. 9, 1993

[54] SALICYLALDEHYDE DERIVATIVES AND SALICYCLIC ACID DERIVATIVES AND THEIR SULFUR ANALOGS, AND THEIR USE AS HERBICIDES AND BIOREGULATORS

[75] Inventors: Uwe J. Vogelbacher, Ludwigshafen; Karl Eicken, Wachenheim; Joachim Rheinheimer, Ludwigshafen; Norbert Goetz, Worms; Albrecht Harreus; Gerhard Paul, both of Ludwigshafen; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 788,859

[22] Filed: Nov. 7, 1991

Related U.S. Application Data

[62] Division of Ser. No. 537,129, Jun. 13, 1990, Pat. No. 5,085,686.

[30] Foreign Application Priority Data

Jun. 14, 1989 [DE] Fed. Rep. of Germany ....... 3919435

[51] Int. Cl.$^5$ ................ C07D 251/26; C07D 251/20; A01N 43/66
[52] U.S. Cl. .................... 504/219; 544/218; 544/219; 504/230; 504/227
[58] Field of Search ..................... 71/93; 544/219, 218

[56] References Cited

FOREIGN PATENT DOCUMENTS 336494 10/1989 European Pat. Off. .
13065 9/1991 World Int. Prop. O. .

*Primary Examiner*—John M. Ford
*Attorney, Agent, or Firm*—Keil & Weinkauf

[57] ABSTRACT

Salicylaldehyde derivatives and salicylic acid derivatives of the formula I

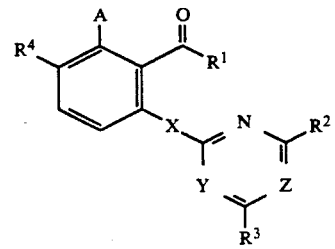

where A is an unsubstituted or substituted phenyl radical, an unsubstituted or substituted 5-membered heteroaromatic radical having from 2 to 4 nitrogen atoms or two nitrogen atoms and additionally one sulfur or oxygen atom or an unsubstituted or substituted thienyl, pyridyl, naphthyl, quinolyl, indazolyl or benzotriazolyl radical, X is oxygen or sulfur, and the radicals $R^1$ to $R^4$ have the meanings given in the specification, processes and intermediates for their production, and their use as herbicides and bioregulators.

15 Claims, No Drawings

SALICYLALDEHYDE DERIVATIVES AND SALICYCLIC ACID DERIVATIVES AND THEIR SULFUR ANALOGS, AND THEIR USE AS HERBICIDES AND BIOREGULATORS

This is a divisional of application Ser. No. 537,129, filed Jun. 13, 1990 now U.S. Pat. No. 5,085,686.

The present invention relates to salicylaldehyde derivatives and salicylic acid derivatives and their sulfur analogs of the formula I

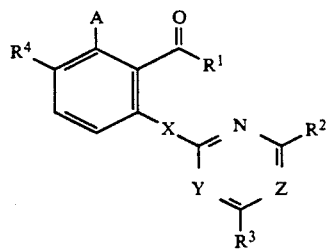

where
$R^1$ is hydrogen;
succinyliminooxy;
a 5-membered heteroaromatic radical containing from one to three nitrogen atoms which may carry from one to four halogen atoms and/or one or two of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio;
a radical —$OR^5$ or a radical $ON=CR^6R^7$, where
$R^5$ is hydrogen, an alkali metal cation, one equivalent of an alkaline earth metal cation or an organic ammonium ion;
$C_3-C_{12}$-cycloalkyl which may carry from one to three $C_1-C_4$-alkyl radicals;
$C_1-C_{10}$-alkyl which may carry from one to five halogen atoms and/or one of the following radicals: $C_1-C_4$-alkoxy, $C_1-C_4$-alkylthio, cyano, $C_1-C_8$-alkylcarbonyl, $C_1-C_8$-alkoxycarbonyl, $C_3-C_{12}$-cycloalkyl, phenyl, phenoxy or phenylcarbonyl, where the aromatic radicals may in turn carry from one to five halogen atoms and/or from one to three of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio; $C_1-C_{10}$-alkyl which may carry from one to five halogen atoms and carries one of the following radicals: a 5-membered heteroaromatic radical containing from 1 to 3 nitrogen atoms which may carry from one to four halogen atoms and/or one or two of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio;
$C_2-C_6$-alkyl which carries one of the following radicals in the 2-position: $C_1-C_6$-alkoxyimino, $C_3-C_6$-alkenyloxyimino, $C_3-C_6$-haloalkenyloxyimino or benzyloxyimino; $C_3-C_6$-alkenyl or $C_3-C_6$-alkynyl, where these groups may in turn carry from one to five halogen atoms;
phenyl which is unsubstituted or monosubstituted to trisubstituted by $C_1-C_4$-alkyl or by $C_1-C_4$-alkoxy or monosubstituted to pentasubstituted by halogen;
$R^6$ and $R^7$ are each $C_1-C_{20}$-alkyl which may carry phenyl, $C_1-C_4$-alkoxy and/or $C_1-C_4$-alkylthio, or are each phenyl or together form a $C_3-C_{12}$-alkylene chain which may carry from one to three $C_1-C_3$-alkyl groups;
$R^2$ and $R^3$ are each $C_1-C_4$-alkyl, $C_1-C_4$-haloalkyl, $C_1-C_4$-alkoxy, $C_1-C_4$-haloalkoxy and/or $C_1-C_4$-alkylthio;
X is oxygen or sulfur;
Y and Z are each nitrogen or a methine group =CH—;
$R^4$ is hydrogen, halogen, $C_1-C_4$-alkyl, cyano or $C_1-C_4$-haloalkyl;
A is an unsubstituted or monosubstituted to trisubstituted, or with halogen as substituent, monosubstituted to pentasubstituted phenyl radical

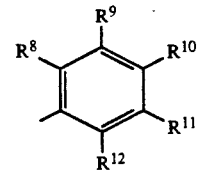

where $R^8$ to $R^{12}$ are each hydrogen, halogen, cyano or nitro;
$C_3-C_6$-alkenyl, $C_3-C_6$-alkenyloxy, $C_3-C_6$-alkynyloxy or $C_3-C_6$-alkynyl, where these groups may in turn carry from one to five halogen atoms;
di-$C_1-C_4$-alkylamino or $C_3-C_8$-cycloalkyl which may carry from one to three $C_1-C_4$-alkyl radicals;
$C_1-C_{10}$-alkoxycarbonyl or $C_1-C_4$-alkylthio; phenoxy, where the aromatic radical may carry from one to five halogen atoms and/or from one to three of the following radicals: $C_1-C_4$-alkyl, $C_1-C_4$-haloalkyl; $C_1-C_4$-haloalkoxy, $C_1-C_4$-alkoxy or $C_1-C_4$-alkylthio; and
$C_1-C_{10}$-alkyl or alkoxy which may carry from one to five halogen atoms and/or one of the following radicals: $C_1-C_4$-alkoxy, $C_1-C_4$-alkylthio, phenyl or phenoxy, where the aromatic radicals may in turn carry from one to five halogen atoms and/or from one to three of the following radicals: $C_1-C_4$-alkyl, $C_1-C_4$-haloalkyl, $C_1-C_4$-haloalkoxy or $C_1-C_4$-alkylthio;
or A is a 5-membered heteroaromatic radical having from 2 to 4 nitrogen atoms or one or two nitrogen atoms and additionally one sulfur or oxygen atom in the ring, which may carry from one to three halogen atoms and/or from one to three of the following radicals: nitro, cyano, $C_1-C_4$-alkyl, $C_1-C_4$-alkylthio, $C_1-C_4$-haloalkyl or phenyl which is unsubstituted or substituted by from one to three halogen atoms and/or from one to three methyl groups;
thienyl which may carry from one to three halogen atoms and/or from one to three of the following radicals: $C_1-C_4$-alkyl, $C_1$- or $C_2$-haloalkyl or nitro;
pyridyl which may carry from one to three halogen atoms and/or from one to three of the following radicals: $C_1-C_4$-alkyl, $C_1$- or $C_2$-haloalkyl or nitro;
a naphthyl, quinolyl, indazolyl or benzotriazolyl radical, each of which may carry from one to three halogen atoms and/or from one to three of the following radicals: $C_1-C_4$-alkyl or $C_1$- or $C_2$-haloalkyl,
and environmentally compatible salts of the compounds I.

The present invention furthermore relates to the processes for the preparation of the compounds I and their use as herbicides and growth regulators, and to novel salicylic acid derivatives of the formula II'

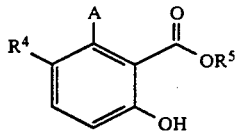

as intermediates for the preparation of the compounds I.

In the formula II', $R^5$ is hydrogen, an alkali metal cation, one equivalent of an alkaline earth metal cation or an organic ammonium ion;

$C_1$–$C_{10}$-alkyl which may carry from one to five halogen atoms and/or one of the following radicals: $C_1$–$C_4$-alkoxy, $C_1$–$C_4$-alkylthio, phenyl or phenoxy, where the phenyl radicals may each carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$R^4$ is hydrogen, halogen, $C_1$–$C_4$-alkyl, cyano or $C_1$–$C_4$-haloalkyl;

A is a monosubstituted to trisubstituted or, where the substituent is halogen, monosubstituted to pentasubstituted phenyl radical

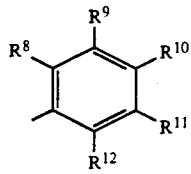

where $R^8$ to $R^{12}$ is hydrogen, halogen, cyano or nitro;

$C_3$–$C_6$-alkenyl, $C_3$–$C_6$-alkenyloxy, $C_3$–$C_6$-alkynyloxy or $C_3$–$C_6$-alkynyl, where these groups in turn may carry from one to five halogen atoms;

di-$C_1$–$C_4$-alkylamino or $C_3$–$C_8$-cycloalkyl which may carry from one to three $C_1$–$C_4$-alkyl radicals;

$C_1$–$C_{10}$-alkoxycarbonyl or $C_1$–$C_4$-alkylthio;

phenoxy, where the aromatic radical may carry from one to five halogen atoms and/or from one to three of the following radicals: $C_1$–$C_4$-alkyl, $C_1$–$C_4$-haloalkyl, $C_1$–$C_4$-haloalkoxy, $C_1$–$C_4$-alkoxy or $C_1$–$C_4$-alkylthio;

a $C_1$–$C_{10}$-alkyl or alkoxy group which may carry from one to five halogen atoms and/or one of the following radicals:

$C_1$–$C_4$-alkoxy, $C_1$–$C_4$-alkylthio, phenyl or phenoxy, where the aromatic radicals may in turn carry from one to five halogen atoms and/or from one to three of the following radicals: $C_1$–$C_4$-alkyl, $C_1$–$C_4$-haloalkyl, $C_1$–$C_4$-haloalkoxy or $C_1$–$C_4$-alkylthio;

with the proviso that $R^5$ is not hydrogen or alkyl when all radicals $R^8$ to $R^{12}$ are hydrogen;

a 5-membered heteroaromatic radical having from two to four nitrogen atoms or one or two nitrogen atoms and additionally a sulfur or oxygen atom in the ring, which may carry from one to three halogen atoms and/or from one to three of the following radicals: nitro, cyano, $C_1$–$C_4$-alkyl, $C_1$–$C_4$-alkylthio, $C_1$–$C_4$-haloalkyl or phenyl which is unsubstituted or substituted by from one to three halogen atoms and/or one to three methyl groups;

thienyl which may carry from one to three halogen atoms and/or from one to three of the following radicals: $C_1$–$C_4$-alkyl, $C_1$- or $C_2$-haloalkyl or nitro;

pyridyl which may carry from one to three halogen atoms and/or from one to three of the following radicals: $C_1$–$C_4$-alkyl, $C_1$- or $C_2$-haloalkyl or nitro; with the proviso that a 3-pyridyl radical carries one or more of the stated substituents;

a naphthyl, quinolyl, indazolyl or benzotriazolyl radical, each of which may carry from one to three halogen atoms and/or from one to three of the following radicals: $C_1$–$C_4$-alkyl or $C_1$- or $C_2$-haloalkyl.

In the literature (EP-A 223 406, EP-A 249 708, EP-A 287 072 and EP-A 287 079) describes herbicidal substituted salicylic acids and their sulfur analogs. However, their action is unsatisfactory.

It is an object of the present invention to provide novel salicylic acid derivatives or their sulfur analogs having improved herbicidal properties and possessing plant growth-regulating properties.

We have found that this object is achieved by the compounds of the formula I, defined at the outset. We have also found processes for the preparation of the compounds I and methods for controlling undesirable plant growth using the compounds I. We have furthermore found that salicylic acid derivatives of the general formula I defined above have excellent plant growth-regulating properties. The novel salicylic acid derivatives II' have been found as intermediates for the preparation of the compounds I.

Compounds of the formula I are obtained, for example, by reacting an appropriately substituted salicylic acid derivative of the formula II, which in specific cases is known or can be prepared by conventional methods starting from known intermediates, with an appropriate compound of the formula III in the presence of a base.

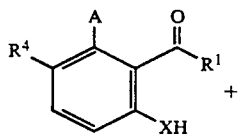

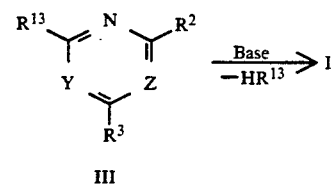

In formula III, $R^{13}$ is a conventional nucleofugic leaving group, for example halogen, such as chlorine, bromine or iodine, aryl- or alkylsulfonyl, such as toluenesulfonyl or methylsulfonyl, or another equivalent leaving group. Compounds of the formula III having a reactive substituent $R^{13}$ are known or are readily obtainable on the basis of the general technical knowledge. Suitable bases are alkali metal or alkaline earth metal hydrides, such as NaH or $CaH_2$, alkali metal hydroxides, such as NaOH and KOH, alkali metal alcoholates, such as potassium tert-butylate, alkali metal carbonates, such as $Na_2CO_3$ and $K_2CO_3$, alkali metal amides, such as $NaNH_2$ and lithium dissopropylamide, or tertiary amines. When an inorganic base is used, a phase transfer catalyst may be added if it promotes conversion.

Where the compounds of the formula I prepared in the manner described are carboxylic acids (i.e. when $R^1$ is hydroxyl), they can also be converted into other compounds described, for example by first converting the carboxylic acid in a conventional manner into an activated form, such as a halide or imidazolide, and then reacting this with the corresponding hydroxy compound. These two steps can also be simplified, for example, by allowing the carboxylic acid to act on the hydroxy compound in the presence of a water-eliminating agent, such as a carbodiimide.

When X is oxygen and A is a heteroaromatic or aromatic radical bonded via a carbon atom, the intermediates of the formula II can be synthesized according to the scheme below, from a 1,3-dicarbonyl compound IV (where $R^5$ is unsubstituted or phenyl-substituted $C_1$-$C_{10}$-alkyl, in particular $C_1$-$C_4$-alkyl) and an $\alpha,\beta$-unsaturated ketone V:

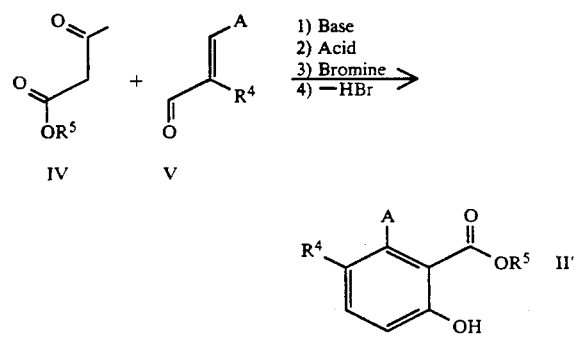

(A = heteroaromatic or aromatic radical bonded via carbon atom)

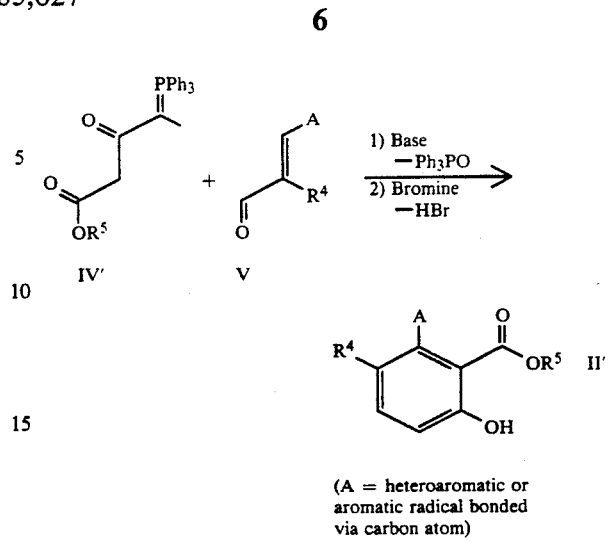

(A = heteroaromatic or aromatic radical bonded via carbon atom)

The compounds IV, IV' and V are generally known or can readily be prepared by conventional processes. Suitable bases are the abovementioned compounds. Suitable acids are strong acids, for example hydrochloric acid, hydrobromic acid, tetrafluoboric acid, toluenesulfonic acid or trifluoroacetic acid. Elimination of hydrogen bromide can be carried out thermally or in the presence of a base, for example an organic amine.

If, in formula II, A is a heteroaromatic radical bonded via a nitrogen atom and X is oxygen, this intermediate can be synthesized according to the following scheme:

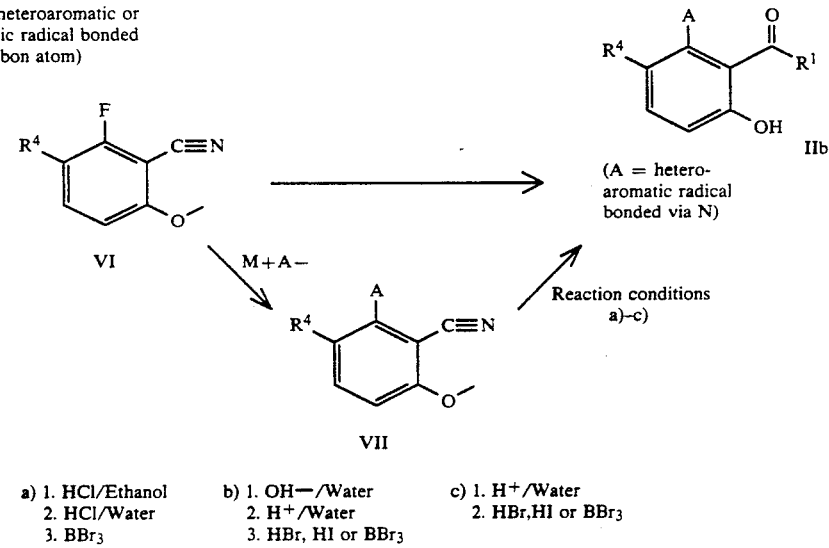

Alternatively, the intermediates of the formula II' can also be prepared according to the scheme below, from a methylenephosphorane IV' and an $\alpha,\beta$-unsaturated ketone V:

$M+A-$ is the particular alkali metal azolide. Suitable alcohols for the cleavage of the nitrile VII in variant a) are, in particular, $C_1$-$C_4$-alkyl alcohols.

The intermediates of the formula II which are prepared as described above are usually obtained as alkyl esters. These can be hydrolyzed by the known methods to give the carboxylic acids. The latter can then be converted by conventional methods into various esters, which are required for the preparation of active ingredients of the formula I as claimed in claim 1.

Alternatively, the intermediates of the formula VII can also be reacted by generally known methods with alkali metal or tetraalkylammonium hydroxides to give the corresponding amides, and then with mineral acids, for example concentrated hydrochloric acid, to give the carboxylic acids, and then with concentrated hydrobromic acid to form the salicylic acids IIb. These steps can, if required, be carried out without isolating the intermediates.

Because of their herbicidal activity, preferred compounds I are those in which $R^1$ is hydrogen, succinyliminooxy, a 5-membered hetaryl radical, such as pyrrolyl, pyrazolyl, imidazolyl and triazolyl, in particular imidazolyl or pyrazolyl, where the aromatic radical is bonded via nitrogen and in turn may carry from one to four halogen atoms as stated above, in particular fluorine and chlorine and/or one or two of the following radicals:

alkyl, such as methyl, ethyl, propyl, 1-methylethyl, butyl, 1-methylpropyl, 2-methylpropyl or 1,1-dimethylethyl, preferably methyl, ethyl or 1-methylethyl, haloalkyl, such as fluoromethyl, difluoromethyl, trifluoromethyl, chlorodifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl or trifluoromethyl, 2,2,2-trifluoroethyl or pentafluoroethyl, alkoxy as stated above, of one to four carbon atoms, haloalkoxy, such as difluoromethyoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy, and/or alkylthio, such as methylthio, ethylthio, propylthio, 1-methylethylthio, butylthio, 1-methylpropylthio, 2-methylpropylthio or 1,1-dimethylethylthio, in particular methylthio or ethylthio;

a radical $OR^5$, where $R^5$ is hydrogen, a cation of an alkali metal or a cation of an alkaline earth metal, such as lithium, sodium, potassium, calcium, magnesium or barium, or an environmentally compatible organic ammonium ion;

alkyl, in particular methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl and octyl, which may carry from one to five of the abovementioned halogen atoms, in particular fluorine and chlorine, and/or one of the following radicals:

cyano, alkoxy or alkylthio of one to four carbon atoms, as stated above, in particular methoxy, ethoxy, 1-methylethoxy or methylthio;

alkylcarbonyl, in particular methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

alkoxycarbonyl, such as methoxycarbonyl, ethoxycarbonyl, propoxycarbonyl, 1-methylethoxycarbonyl, butyloxycarbonyl, 1-methylpropyloxycarbonyl, 2-methylpropoxycarbonyl, 1,1-dimethylethoxycarbonyl, n-pentyloxycarbonyl, 1-methylbutyloxycarbonyl, 2-methylbutoxycarbonyl, 3-methylbutoxycarbonyl, 1,2-dimethylpropoxycarbonyl, 1,1-dimethylpropoxycarbonyl, 2,2-dimethylpropoxycarbonyl, 1-ethylpropoxycarbonyl, n-hexyloxycarbonyl, 1-methylpentyloxycarbonyl, 2-methylpentyloxycarbonyl, 3-methylpentyloxycarbonyl, 4-methylpentyloxycarbonyl, 1,2-dimethylbutoxycarbonyl, 1,3-dimethylbutoxycarbonyl, 2,3-dimethylbutoxycarbonyl, 1,1-dimethylbutoxycarbonyl, 2,2-dimethylbutoxycarbonyl, 3,3-dimethylbutoxycarbonyl, 1,1,2-trimethylpropoxycarbonyl, 1,2,2-trimethylpropoxycarbonyl, 1-ethylbutoxycarbonyl, 2-ethylbutoxycarbonyl, 1-ethyl-2-methylpropoxycarbonyl, n-heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-ethylpentyloxycarbonyl, 2-ethylpentyloxycarbonyl, 1-propylbutoxycarbonyl or octyloxycarbonyl, in particular methoxycarbonyl, ethoxycarbonyl, 1-methylethoxycarbonyl or 1-methylpropoxycarbonyl;

phenyl, phenoxy or phenylcarbonyl, where these aromatic radicals may in turn carry from one to five halogen atoms as stated above, in particular fluorine, chlorine or bromine, and/or from one to three of the following radicals:

alkyl, haloalkyl, alkoxy, haloalkoxy and/or alkylthio, each of one to four carbon atoms, as stated above in general and in particular, or $C_1$-$C_{10}$-alkyl, as stated above, which may carry from one to five halogen atoms, such as fluorine, chlorine, bromine or iodine, in particular fluorine or chlorine, and additionally carries one of the following radicals:

a 5-membered hetaryl radical having from one to three nitrogen atoms, as stated above for $R^1$;

$C_2$-$C_6$-alkyl, in particular $C_2$-$C_4$-alkyl, which is substituted in the 2-position by $C_1$-$C_6$-alkoxyimino, e.g. methoxy-, ethoxy- or propoxyimino; $C_3$-$C_6$-alkenyloxyimino, such as 2-propenyloxyimino, 2-butenyloxyimino or 3-butenyloxyimino; $C_3$-$C_6$-haloalkenyloxyimino, such as 3,3-dichloro-2-propenyloxyimino, 2,3,3-trichloro-2-propenyloxyimino or benzyloxyimino;

alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl;

alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, and 1-ethyl-1-methyl-2-propynyl, preferably 2-propynyl, 2-butynyl, 1-methyl-2-propynyl and 1-methyl-2-butynyl, in particular 2-propynyl, where these alkenyl and alkynyl groups may carry from one to five of the halogen atoms stated above in general and in particular; $C_3-C_{12}$-cycloalkyl, in particular $C_3-C_6$-cycloalkyl, such as cyclopropyl, cyclobutyl, cyclopentyl, cyclohexyl, which is unsubstituted or substituted by one to three $C_1-C_4$-alkyl radicals;

phenyl which is unsubstituted or monosubstituted to trisubstituted by $C_1-C_4$-alkyl or -alkoxy, such as methyl, ethyl, propyl, butyl, methoxy, ethoxy, or phenyl which is substituted by one to five halogen atoms, e.g. chlorine or fluorine;

a radical ON=$CR^6R^7$, where $R^6$ and $R^7$ are each straight-chain or branched $C_1-C_{20}$-alkyl, preferably $C_1-C_{15}$-alkyl, in particular $C_1-C_9$-alkyl, which may carry a phenyl, a $C_1-C_4$-alkoxy or a $C_1-C_4$-alkylthio radical, or are each phenyl or together form $C_3-C_{12}$-alkylene, preferably $C_4-C_7$-alkylene, which may carry from one to three $C_1-C_3$-alkyl groups, preferably methyl or ethyl;

$R^2$ and $R^3$ are each in general and in particular the alkyl groups, haloalkyl groups, alkoxy groups, haloalkoxy groups and/or alkylthio groups, each of 1 to 4 carbon atoms, stated for $R^1$;

X is oxygen or sulfur;

Y and Z are each nitrogen or a methine group =CH—;

$R^4$ is hydrogen; halogen as stated for $R^1$, in particular fluorine, chlorine or bromine;

cyano;

alkyl of one to four, in particular one to three, carbon atoms which is monosubstituted to pentasubstituted by halogen, in particular fluorine or chlorine, for example methyl, ethyl, n-propyl, isopropyl, trichloromethyl and trifluoromethyl;

A is unsubstituted or substituted phenyl, where the substituents $R^8$ to $R^{12}$ are the following: halogen, such as fluorine, chlorine, bromine or iodine; cyano; nitro; unsubstituted or halogen-substituted alkenyl, alkenyloxy, alkynyloxy or alkynyl, each of 3 to 6 carbon atoms; di-$C_1-C_4$-alkylamino, such as dimethylamino, diethylamino, dipropylamino, di-1-methylethylamino, dibutylamino, di-1-methylpropylamino, di-2-methylpropylamino, di-1,1-dimethylethylamino, ethylmethylamino, propylmethylamino, 1-methylethylmethylamino or butylmethylamino; unsubstituted or alkyl-substituted cycloalkyl as stated above for $R^5$, alkoxycarbonyl or alkylthio as stated above for $R^5$, unsubstituted or substituted phenoxy as stated under $R^5$, $C_1-C_{10}$-alkyl or alkoxy, in particular $C_1-C_6$-alkyl or alkoxy, preferably $C_1-C_4$-alkyl or alkoxy, which are unsubstituted or substituted by the stated radicals; for example, the following substituted phenyl radicals for A may be mentioned:

2-fluorophenyl, 3-fluorophenyl, 4-fluorophenyl, 2,6-difluorophenyl, 2,4-difluorophenyl, 2-fluoro-4-trifluoromethylphenyl, 2,3-difluorophenyl, 2-chlorophenyl, 3-chlorophenyl, 2-iodophenyl, 2-bromophenyl, 2-chloro-6-fluorophenyl, pentafluorophenyl, pentachlorophenyl, 2,4-dichlorophenyl, 2,6-dichlorophenyl, 2-chloro-4-fluorophenyl, 3,5-dichlorophenyl, 2-chloro-6-methylphenyl, 2,3,5-trichlorophenyl, 2-methylphenyl, 3-methylphenyl, 4-methylphenyl, 2,6-dimethylphenyl, 2,4-dimethylphenyl, 3,5-dimethylphenyl, 2,4,6-trimethylphenyl, 2-chloro-4-methylphenyl, 2-methoxyphenyl, 4-methoxyphenyl, 4-chloro-2-methoxyphenyl, 2-trifluoromethylphenyl, 2,3-dimethyl-4-methoxyphenyl, 4-dimethylamino-2-methylphenyl, 3-cyanophenyl, 3-nitrophenyl, 3-phenoxyphenyl, 3-(3-trifluoromethylphenoxy)phenyl, 3-trifluoromethylphenyl, unsubstituted or substituted 5-membered hetaryl having 2 to 4 nitrogen atoms, as stated for $R^1$, or one or two nitrogen atoms and in addition a sulfur or oxygen atom, such as isoxazolyl, oxazolyl, thiazolyl or thiadiazolyl.

Examples of hetaryl radicals are the following: pyrazol-1-yl, 4-methylpyrazol-1-yl, 3,5-dimethylpyrazol-1-yl, 3,4,5-trimethylpyrazol-1-yl, 4-chloropyrazol-1-yl, 4-phenylpyrazol-1-yl, 4-isopropylpyrazol-1-yl, 4-nitropyrazol-1-yl, imidazol-1-yl, 4,5-dimethylimidazolyl, 2-methyl-4,5-dichloroimidazolyl, 4(5)-nitroimidazol-1-yl, [1,2,4]-triazol-1-yl, 3(5)-methyl-[1,2,4]-triazol-1-yl, [1,2,3]-triazol-1-yl, 4,5-dimethyl-[1,2,3]-triazol-1-yl, [1,2,3,4]-tetrazol-1-yl, 1-methylpyrazol-4-yl, 1-phenylpyrazol-4-yl, 1,3,5-trimethylpyrazol-4-yl, 1-methylpyrazol-5-yl, 1-phenylpyrazol-5-yl, 1-methylpyrazol-3-yl, 1-phenylpyrazol-3-yl, 1-methylimidazol-2-yl, 1-methylimidazol-5-yl, 1-phenylimidazol-5-yl, 1-phenyl-[1,2,3]-triazol-4-yl, isoxazol-5-yl, isoxazol-4-yl, 3-methylisoxazol-5-yl, 3-isopropyl-isoxazol-5-yl, 3-phenylisoxazol-5-yl, oxazol-2-yl, 2-methyloxazol-4-yl, thiazol-4-yl, 2-benzthiazol-4-yl, 4-methylthiazol-2-yl, 4-methylthiazol-5-yl, 4-phenylthiazol-2-yl and 2-phenylthiazol-5-yl.

Unsubstituted or substituted thienyl, pyridyl, naphthyl, quinolyl, indazolyl or benzotriazolyl radicals A are, for example, 2-thienyl, 3-thienyl, 2,3-dichloro-4-thienyl, 2-methyl-5-thienyl, 2-nitro-5-thienyl, 2-pyridyl, 3-pyridyl, 4-pyridyl, 6-methyl-2-pyridyl, 1-naphthyl, quinol-2-yl, quinol-4-yl, quinol-8-yl, 7-chloroquinol-8-yl, 1-indazolyl and 1-benzotriazolyl.

Particularly preferred compounds of the formula I are those in which $R^2$ and $R^3$ are each methoxy, methyl, difluoromethoxy or chlorine, $R^4$ is hydrogen or methyl, X is oxygen, Y is nitrogen, Z is a methine group and $R^1$ and A each have the meanings stated in the claim.

Examples of salts of compounds of the formula I are environmentally tolerated salts such as alkali metal salts, especially the potassium or sodium salts, alkaline earth metal salts, especially the calcium, magnesium or barium salts, manganese, copper, zinc or iron salts, and ammonium, phosphonium, sulfonium or sulfoxonium salts, for example ammonium salts, tetraalkylammonium salts, benzyltrialkylammonium salts, trialkylsulfonium salts and trialkylsulfoxonium salts.

The herbicidal and growth-regulating agents I, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are suitable for the preparation of solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methyl-pyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are employed in a purity of 90 to 100, and preferably 95 to 100, % (according to the NMR spectrum).

Examples of formulations are as follows:

I. 90 parts by weight of compound no. 1.004 is mixed with 10 parts by weight of N-methyl-alpha-pyrrolidone. A mixture is obtained which is suitable for application in the form of very fine drops.

II. 20 parts by weight of compound no. 1.005 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.024 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.063 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 2.003 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 2.004 is intimately mixed with 97 parts by weight of particulate kaolin. A dust is obtained containing 3% by weight of the active ingredient.

VII. 30 parts by weight of compound no. 1.004 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.024 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.005 to 0.5, kg of active ingredient per hectare.

The growth-regulating salicylic acid derivatives of the formula I may exercise a variety of influences on practically all plant development stages, and are therefore used as growth regulators. The diversity of action of growth regulators depends especially on a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitation, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

In fruit and other trees, pruning costs can be reduced with growth regulators. With growth regulators, it is also possible to break up the alternate breeding rhythm of fruit trees.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The salicylic acid derivatives of the formula I may raise the yield by influencing plant metabolism or by promoting or inhibiting vegetative and/or generative plant growth.

C. It is also possible with growth regulators to shorten or lengthen growth states and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a dressing), but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.01 to 10, g per kg of seed are generally required. For foliage and soil treatment, amounts of from 0.001 to 10, preferably from 0.01 to 3, and especially from 0.01 to 0.5, kg/ha are generally considered to be sufficient.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.01 to 1.0, kg of active ingredient per hectare.

In view of the numerous application methods possible, the compounds according to the invention, or agents containing them, may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the compounds of the formula I according to the invention may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, (hetero)-aryloxyphenoxypropionic acid derivatives (salts, esters, amides), etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The methods described in the Synthesis Examples below were used, with appropriate modification of the starting compounds, to obtain further compounds I. The compounds thus obtained are listed in the Tables below, together with physical data. Compounds without this data can be synthesized similarly from the corresponding starting compounds. The structures shown in the Table describe particularly preferred active ingredients of the formula I.

EXAMPLE 1

Methyl 3-(4,6-dimethoxypyrimidin-2-yl)-oxybiphenyl-2-carboxylate (compound No. 1005):

a) Methyl 6-phenylsalicylate:

Variant 1

58 g (0.5 mol) of methyl acetoacetate are added to a solution of 0.5 g of sodium hydride in 100 ml of dry ethanol, 66 g (0.5 mol) of cinnamaldehyde are rapidly added dropwise and the mixture is stirred for about 10 h at room temperature. The mixture is then saturated at 0° C. with dry HCl gas and then stirred for a further 1 day at room temperature (20° C.). The solvent is removed and the remaining residue is distilled under reduced pressure, HCl gas initially being liberated. Fractions passing over from 115° to 165° C./0.2 mbar are combined and are chromatographed over silica gel (elution with toluene/-cyclohexane). 33.7 g of a yellow oil are obtained as an intermediate. This is dissolved in 150 ml of methylene chloride, and a solution of 22.9 g (0.14 mol) of bromine in 150 ml of glacial acetic acid is added rapidly at 0° C., and the mixture is slowly heated up and is refluxed for one hour. The reaction solution is poured into 200 ml of methylene chloride and 500 ml of water. The organic phase is separated off and worked up in a conventional manner. A yellow solid is obtained as an intermediate, which is dissolved in 400 ml of methyl tert-butyl ether for further processing. 55 g (0.56 mol) of triethylamine are added and the mixture is refluxed for 5 h. Thereafter, 300 ml of water are added, and the organic phase is separated off and worked up in a conventional manner. The residue is distilled at 100°–114° C./0.2 mbar. Yield: 11.9 g.

Variant 2

8.55 g (0.3 mol) of 85% sodium hydride are added a little at a time to a solution of 57 g (0.15 mol) of methyl 4-(triphenylphosphoranylidene)-acetoacetate in 700 ml of tetrahydrofuran under a nitrogen atmosphere and the mixture is then heated to about 35° C. At this temperature, 20 g (0.15 mol) of cinnamaldehyde are added a little at a time, followed by 5–10 drops of water, and the initially exothermic reaction requires cooling. The reaction is continued at 35° C. until the ylide has been completely converted (TLC check, about 12–14 h). The reaction mixture is then rendered acidic with 10% strength hydrochloric acid and, after the addition of 1 l of water, is extracted with four times 150 ml of ether. The combined ether phases are extracted by shaking in 200 ml of water and 200 ml of saturated sodium chloride solution, dried over sodium sulfate and evaporated down. The remaining blackish brown residue is taken up in 400 ml of methyl tert-butyl ether and boiled for several hours. After cooling, it is filtered off from the insoluble residue (triphenylphosphine oxide), and the filtrate is evaporated down. The remaining oil is purified by chromatography over silica gel (mobile phase: toluene/ethyl acetate with gradually increasing ethyl acetate content). All fractions before the triphenylphosphine oxide are combined and are brominated, aromatized and worked up similarly to the above method. 14.5 g of product are obtained.

b) Methyl 3-(4,6-dimethoxypyrimidin-2-yl)-oxybiphenyl-2-carboxylate:

11.4 g (0.05 mol) of methyl 3-hydroxybiphenyl-2-carboxylate in 50 ml of dry dimethylformamide are initially taken, and 1.5 g (0.05 mol) of 80% strength sodium hydride are added a little at a time at from 0° to 5° C., while stirring. 10.9 g (0.05 mol) of 4,6-dimethoxy-2-methylsulfonylpyrimidine are then added at room temperature, the mixture is heated to 90° C. and stirring is continued at this temperature for 6 h. The solution thus obtained is poured into water. The mixture is extracted with methylene chloride and the extract is washed with water, dried over sodium sulfate and evaporated down. The crude product can be further purified by column chromatography using toluene/ethyl acetate, with the result that 9.6 g of a solid of melting point 98°–102° C. is obtained.

For example, the following compounds can also be prepared similarly to a) or b):

Methyl 6-(3,5-dichlorophenyl)-salicylate, $^1$H-NMR (CDCl$_3$: δ=3.58 (s; 3H); 6.70 (d; 1H); 7.05 (d; 1H); 7.10 (d; 2H); 7.25–7.40 (m; 2H); 10.85 (s; 1H).

Methyl 6-(2,4-dichlorophenyl)-salicylate, $^1$H-NMR (CDCl$_3$: δ=3.58 (s; 3H); 6.65 (d; 1H); 7.0–7.5 (m; 5H); 11.1 (s; 1H).

Methyl 2-(4,6-dimethoxypyrimidin-2-yl)-oxy-6-(3,5-dichlorophenyl)-benzoate (compound No. 1063), mp. 133°–137° C.

Methyl 2-(4,6-dimethoxypyrimidin-2-yl)-oxy-6(2,4-dichlorophenyl)-benzoate (compound No. 1024), mp. 99°–100° C.

EXAMPLE 2

General method for the preparation of the salicylic acid derivatives of the formula I:

0.073 mol of the particular aromatic 2-hydroxycarboxylic acid is dissolved in 320 ml of dry dimethyl sulfoxide, and 16.4 g (0.146 mol) of potassium tertbutylate are added a little at a time, the temperature of the reaction mixture increasing to about 30° C. The mixture is cooled to room temperature, 16.0 g (0.073 mol) of 4,6-dimethoxy-2-methylsulfonylpyrimidine are added and stirring is contiuned for about 1 h at room temperature. The reaction mixture is poured into about 2 l of cold water, acidified with hydrochloric acid and extracted with methyl tert-butyl ether. After the usual working up, the remaining crude product can, if required, be purified by stirring with a suitable solvent or by chromatography over silica gel.

EXAMPLE 3

General method for the preparation of the salicylic acid derivatives of the formula I:

5.1 g of potassium hydroxide and 0.08 mol of the particular 2-hydroxycarboxylic acid aredissolved in 80 ml of methanol, and the solution is stirred at room temperature for 10 minutes and evaporated down under reduced pressure. Thereafter, toluene is added repeatedly to effect drying and is evaporated at 50° C. under reduced pressure. The pale red powder thus obtained is taken up in 300 ml of dimethyl sulfoxide, and 2.9 g of 80% strength sodium hydride are added a little at a time at room temperature, gas evolution occurring. When gas is no longer evolved, a solution of 17.4 g of 4,6-dimethoxy-2-methylsulfonylpyrimidine (or an equivalent amount of the particular pyridine, pyrimidine or triazine derivative used) in 80 ml of dimethy sulfoxide is added dropwise and stirring is continued for 0.5 h. The mixture is poured into 2 l of water, neutralized with acetic acid and washed with methylene chloride. It is then rendered strongly acidic with hydrochloric acid and extracted several times with methyl tert-butyl ether. The organic phase is dried over sodium sulfate and the solvent is evaporated under reduced pressure. The remaining substance can be purified by chromatography over silica gel.

EXAMPLE 4

General method for the preparation of aromatic carboxylic oxime esters or similar compounds of the formula I:

3.2 mmol of the particular aromatic 2-(4,6-dimethoxypyrimidin-2-yl)-oxycarboxylic acid in 20 ml of dimethoxyethane are initially taken and 3.2 mmol of sodium hydride are added, gas evolution occurring immediately. The mixture is stirred for 1 h at room temperature and cooled to 0° C., and 3.5 mmol of oxalyl chloride are added. Stirring is continued for 1 h at 0° C., after which about 30% of the solvent are evaporated under reduced pressure in order to remove the excess oxalyl chloride. 4.2 mmol of the particular oxime or of a comparable hydroxy compound dissolved in 10 ml of dimethoxyethane and then 3.2 mmol of pyridine are added at 0° C., and the mixture is warmed to room temperature in the course of 1 h. The mixture is poured into 120 ml of cold water and extracted with methylene chloride. The organic phase is dried over sodium sulfate and evaporated down under reduced pressure. The remaining substance can be further purified by chromatography over silica gel.

EXAMPLE 5

Ethyl 2-(4,6-dimethoxypyrimidin-2-yl)-oxy-6-(pyrazol-1-yl)-benzoate (compound No. 2004):

a) 2-Methoxy-6-(pyrazol-1-yl)-benzonitrile:

A solution of 0.273 mol of sodium pyrazolide (prepared from equimolar amounts of pyrazole and sodium hydride) in 140 ml of N,N-dimethylethyleneurea is added dropwise at 50° C., under nitrogen, to a solution of 41.2 g (0.273 mol) of 2-methoxy-6-fluorobenzonitrile (preparation: J. Heterocycl. Chem. 25 (1988), 1173) in 50 ml of N,N-dimethylethyleneurea and the mixture is stirred at 60° C. for 2h. After the mixture has been cooled and stirred into 4 l of ice water and the precipitated crystals have been filtered off under suction and dried, 37.1 g of the product of melting point 93°-94° C. are obtained.

b) O-ethylimino 2-methoxy-6-(pyrazol-1-yl)-benzoate:

37.1 g (0.186 mol) of 2-methoxy-6-(pyrazol-1-yl)-benzonitrile are introduced at 0° C., while stirring, into 68.0 g of a 38% strength solution of dry HCl gas in ethanol in the absence of moisture. After dilution with 20 ml of ethanol, the mixture is stirred for 48 h at room temperature, poured into 500 ml of ice water and brought to a pH of 7 by the addition of 2N sodium hydroxide solution followed by saturated sodium bicarbonate solution. After the precipitated crystals have been filtered off under suction and dried, 30.3 g of the product of melting point 72°-73° C. are obtained.

c) Ethyl 2-methoxy-6-(pyrazol-1-yl)-benzoate:

29.0 g (0.118 mol) of O-ethylimino 2-methoxy-6-(pyrazol-1-yl)-benzoate and 300 ml of hydrochloric acid are stirred for 16 h at 50° C. After cooling, the reaction mixture is extracted with three times 100 ml of methylene chloride. The extract is evaporated down to give 16.7 g of residue, which is chromatographed over silica gel using 9:1 toluene/ethyl acetate. 13.4 g of the product of melting point 159°-163° C. are obtained.

d) Ethyl 6-(pyrazol-1-yl)-salicylate:

200 ml (0.2 mol) of 1 molar boron tribromide solution are added dropwise to a solution of 15.3 g (0.062 mol) of ethyl 2-methoxy-6-(pyrazol-1-yl)-benzoate in 140 ml of methylene chloride at from 20° to 25° C. Stirring is carried out for about 10 h at room temperature, after which 160 ml of ethanol are added dropwise at 0° C. Stirring is continued for 15 minutes, after which the solvent is substantially removed at 30° C. under reduced pressure and the residue is stirred with 200 ml of water. The residue is extracted with three times 70 ml of diethyl ether, the extract is evaporated down and the crude product is chromatographed over silica gel using toluene/ethyl acetate. 8.7 g of product are obtained as an oil. $^1$H-NMR (selected signals): $\delta = 0.98$ (t); 4.10 (q); 6.38; 6.90; 7.10; 7.45 (t); 7.60; 7.70; 10.70 (s).

From these compounds, it is possible to obtain 6-(pyrazol-1-yl)-salicylic acid by hydrolysis with dilute sodium hydroxide solution (melting point: 175°-179° C.).

e) Methyl 2-(4,6-dimethoxypyrimidin-2-yl)-oxy-6-(pyrazol-1-yl)-benzoate:

0.46 g (0.015 mol) of 80% strength sodium hydride is added at 10° C. to 3.48 g (0.015 mol) of ethyl 6-(pyrazol-1-yl)-salicylate dissolved in 25 ml of dry dimethylformamide, and the mixture is stirred at 30° C. for 3 h. Thereafter, 3.27 g (0.015 mol) of 2-methylsulfonyl-4,6-dimethoxypyrimidine are added and stirring is continued for about 12 h at room temperature. The reaction mixture is added to 500 ml of water to which 2.5 ml of orthophosphoric acid were added beforehand. The oil which separates out is taken up in ethyl acetate and dried over sodium sulfate. Evaporation gives 4.0 g of a crystalline crude product, which is further purified by recrystallization from diethyl ether/methyl tert-butyl ether. Melting point 94°-96° C.

EXAMPLE 6

2-(4,6-Dimethoxypyrimidin-2-yl)-oxy-6-(1,2,4-triazol-1yl)-benzoic acid (compound No. 2035)

a) 2-Methoxy-6-(1,2,4-triazol-1-yl)-benzonitrile:

A solution of 30.2 g (0.20 mol) of 2-methoxy-6-fluorobenzonitrile [preparation: J. Heterocycl. Chem. 25 (1988), 1173] in 50 ml of N,N-dimethylformamide is added dropwise at 45°-50° C., under nitrogen, to a solution of 0.21 mol of sodium triazolide (prepared from equimolar amounts of triazol and sodium hydride) in 100 ml of N,N-dimethylformamide, and the mixture is stirred for 2 h at 50° C. After the solvent has been evaporated under reduced pressure, the residue is stirred with 200 ml of ice water, the pH is brought to 6 with a little glacial acetic acid and the solid is filtered off under suction and dried. After the addition of a little ether, 35 g of the product of melting point 169°-171° C. (decomposition) are obtained.

b) 2-Methoxy-6-(1,2,4-triazol-1-yl)-benzamide:

15.0 g (0.075 mol) of 2-methoxy-6-(1,2,4-triazol-1-yl)-benzonitrile are suspended in 300 ml of water, 9.6 (0.015 mol) of 40% strength tetrabutylammonium hydroxide solution are added and the mixture is refluxed for 4 h and evaporated down under reduced pressure. The crude product is further hydrolyzed without additional purification (see C). A sample of the above product isolated from this crude product has a melting point of 140°-150° C. (decomposition).

c) 2-Methoxy-6-(1,2,4-triazol-1-yl)-benzoic acid:

0.116 mol of the above crude 2-methoxy-6-(1,2,4-triazol-1yl)-benzamide are stirred in a mixture of 120 ml of concentrated hydrochloric acid and 60 ml of glacial acetic acid for 5 h at 100° C. The mixture is evaporated down under reduced pressure and the process is repeated with the residue. After further evaporation of the mixture, the residue is dissolved in a little water and the solution is brought to pH 3 with sodium hydroxide solution. 30-40 ml of ethanol are added, after which the precipitate is filtered off under suction and dissolved in methanol. After the solution has been dried and evaporated down, 14.7 g of the above acid of melting point 200°-202° C. (decomposition) are isolated.

d) 6-(1,2,4-triazol-1-yl)-salicylic acid:

9.2 g (0.042 mol) of 2-methoxy-6-(1,2,4-triazol-1-yl)-benzoic acid and 50 ml of hydrobromic acid (47% strength) are stirred for 5 h at 100° C. After the mineral acid has been evaporated under reduced pressure, the residue is stirred with ethanol and the mixture is again evaporated down under reduced pressure. After the residue has been made into a paste with about 20 ml of water, the pH has been brought to 3.5 with sodium hydroxide solution and the solid has been filtered off under suction and dried, 4.6 g of the crude product are obtained; after this crude product has been boiled with 40 ml of ethyl acetate and cooled and the solid has been filtered off under suction, 3.5 g of the above salicylic acid of melting point 214°-215° C. (decomposition) are obtained.

e) 2-(4,6-Dimethoxypyrimidin-2-yl)-oxy-6-(1,2,4-triazonl-1-yl)-benzoic acid:

2.24 g (0.02 mol) of potassium tert-butylate are added a little at a time to 2.05 g (0.01 mol) of 6-(1,2,4-triazol-1-yl)-salicylic acid in 30 ml of dry dimethyl sulfoxide, and the mixture is stirred for 1 h at 40° C. Thereafter, 2.18 g (0.01 mol) of 2-methylsulfonyl-4,6-dimethoxypyrimidine are added at room temperature and stirring is continued for about 20 h at room temperature. The reaction mixture is poured into 450 ml of ice water to which 1 ml of orthophosphoric acid has been added beforehand. After the precipitate has been filtered off under suction, washed with cold water and dried, 2.85 g of the above product of melting point 158°-160° C. are obtained.

TABLE 1

Compounds I in which A is substituted or unsubstituted phenyl

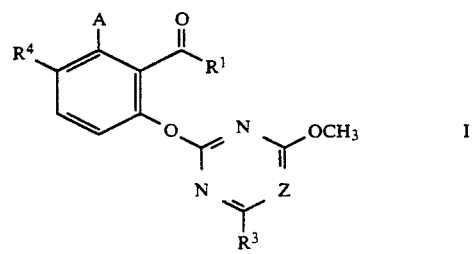

I

| No. | $R^1$ | $R^3$ | $R^4$ | A | Z | Phys. data mp. [°C.] |
|---|---|---|---|---|---|---|
| 1.001 | OH | $OCH_3$ | H | phenyl | N | 120-125 |
| 1.002 | OH | $CH_3$ | H | phenyl | N | |
| 1.003 | $OCH_3$ | $OCH_3$ | H | phenyl | N | |
| 1.004 | OH | $OCH_3$ | H | phenyl | CH | 185-195, decomp. |
| 1.005 | $OCH_3$ | $OCH_3$ | H | phenyl | CH | 98-102 |
| 1.006 | 2-propaniminoxy | $OCH_3$ | H | phenyl | CH | |
| 1.007 | 1-imidazolyl | $OCH_3$ | H | phenyl | CH | |
| 1.008 | methylthiomethoxy | $OCH_3$ | H | phenyl | CH | |
| 1.009 | OH | $OCH_3$ | H | 2-fluorophenyl | CH | 122-128 |
| 1.010 | $OC_2H_5$ | $OCH_3$ | H | 3-fluorophenyl | CH | 52-60 |
| 1.011 | OH | $OCH_3$ | H | 4-fluorophenyl | CH | |
| 1.012 | OH | $OCH_3$ | H | 2,6-difluorophenyl | CH | |
| 1.013 | OH | $OCH_3$ | H | 2,4-difluorophenyl | CH | |
| 1.014 | OH | $OCH_3$ | H | 2-fluoro-4-trifluoromethylphenyl | CH | |
| 1.015 | H | $OCH_3$ | H | 2,3-difluorophenyl | CH | |
| 1.016 | OH | $OCH_3$ | H | 2-chlorophenyl | CH | 129-135 |
| 1.017 | $OC_2H_5$ | $OCH_3$ | H | 2-iodophenyl | CH | |
| 1.018 | methoxyethoxy | $OCH_3$ | H | 2-bromophenyl | CH | |
| 1.019 | OH | $OCH_3$ | H | 2-bromophenyl | CH | |
| 1.020 | OH | $OCH_3$ | H | 2-chlorophenyl | N | |
| 1.021 | OH | $OCH_3$ | H | 2-chloro-6-fluorophenyl | CH | |
| 1.022 | OH | $OCH_3$ | H | pentafluorophenyl | CH | |
| 1.023 | OH | $OCH_3$ | H | 2,4-difluorophenyl | CH | |
| 1.024 | $OCH_3$ | $OCH_3$ | H | 2,4-dichlorophenyl | CH | 99-100 |
| 1.025 | OH | $OCH_3$ | H | 2,6-dichlorophenyl | CH | |
| 1.026 | OH | $OCH_3$ | H | 2-chloro-4-fluorophenyl | CH | |
| 1.027 | OH | $OCH_3$ | H | 3,5-dichlorophenyl | CH | |
| 1.028 | 3-dodecaniminoxy | $OCH_3$ | H | 3,5-dichlorophenyl | CH | |
| 1.029 | OH | $OCH_3$ | H | 2-methylphenyl | CH | 116-118 |
| 1.030 | $OC_2H_5$ | $OCH_3$ | H | 2-methylphenyl | CH | |
| 1.031 | ethylthioethoxy | $OCH_3$ | H | 2-methylphenyl | CH | |
| 1.032 | 1-imidazolyl | $OCH_3$ | H | 2-methylphenyl | CH | |
| 1.033 | OH | $OCH_3$ | H | 2-chloro-6-methylphenyl | CH | |
| 1.034 | OH | $OCH_3$ | H | 3-methylphenyl | CH | 63-67 |
| 1.035 | OH | $OCH_3$ | H | 4-methylphenyl | CH | 50-58 |
| 1.036 | OH | $OCH_3$ | H | 2,6-dimethylphenyl | CH | |
| 1.037 | OH | $OCH_3$ | H | 3,5-dimethylphenyl | CH | |
| 1.038 | OH | $OCH_3$ | H | 2,4,6-trimethylphenyl | CH | 135-143 |
| 1.039 | $OC_2H_5$ | $OCH_3$ | H | 2,4,6-trimethylphenyl | CH | |
| 1.040 | OH | $OCH_3$ | H | 2,4-dimethylphenyl | CH | |
| 1.041 | OH | $OCH_3$ | H | 2-chloro-4-methylphenyl | CH | |

TABLE 1-continued

Compounds I in which A is substituted or unsubstituted phenyl

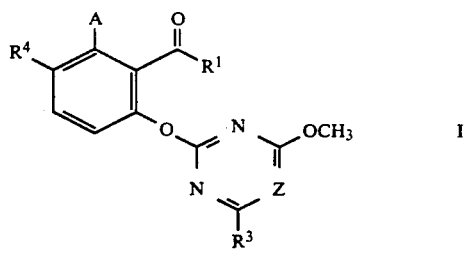

| No. | R¹ | R³ | R⁴ | A | Z | Phys. data mp. [°C.] |
|---|---|---|---|---|---|---|
| 1.042 | OH | OCH₃ | H | 2,3,5-trichlorophenyl | CH | |
| 1.043 | OH | OCH₃ | H | 4-methoxyphenyl | CH | 82-116 |
| 1.044 | OH | OCH₃ | H | 2-methoxyphenyl | CH | 145-149 |
| 1.045 | OH | OCH₃ | H | 4-chloro-2-methoxyphenyl | CH | |
| 1.046 | OH | OCH₃ | H | 2-trifluoromethylphenyl | CH | |
| 1.047 | OH | OCH₃ | H | 2,3-dimethyl-4-methoxyphenyl | CH | |
| 1.048 | OH | OCH₃ | H | 2-dimethylamino-2-methylphenyl | CH | |
| 1.049 | OH | OCH₃ | H | 3-cyanophenyl | CH | |
| 1.050 | OC₂H₅ | OCH₃ | H | 3-nitrophenyl | CH | |
| 1.051 | OH | OCH₃ | H | 3-phenoxyphenyl | CH | |
| 1.052 | OH | OCH₃ | H | 3-(3-trifluoromethylphenoxy)-phenyl | CH | |
| 1.053 | OH | OCH₃ | H | 3-trifluoromethylphenyl | CH | |
| 1.054 | OCH₃ | OCH₃ | H | 3-trifluoromethylphenyl | CH | |
| 1.055 | OH | OCH₃ | H | 3-bromophenyl | CH | |
| 1.056 | OH | OCH₃ | H | 3-chlorophenyl | CH | |
| 1.057 | OH | OCH₃ | H | 4-bromophenyl | CH | 130-131 |
| 1.058 | OH | OCH₃ | H | 4-chlorophenyl | CH | 132-134 |
| 1.059 | OH | OCH₃ | H | 4-trifluoromethylphenyl | CH | 130-131 |
| 1.060 | OH | OCH₃ | H | 3-(3,4-dichlorophenoxy)phenyl | CH | |
| 1.061 | OH | OCH₃ | H | 4-methylthiophenyl | CH | |
| 1.062 | OH | OCH₃ | H | 4-t.-butylphenyl | CH | 73-75 |
| 1.063 | OCH₃ | OCH₃ | H | 3,5-dichlorophenyl | CH | 133-137 |
| 1.064 | 2-(ethoxyimino)-ethoxy | OCH₃ | H | phenyl | CH | |
| 1.065 | 2-(allyloxyimino)-ethoxy | OCH₃ | H | phenyl | CH | |
| 1.066 | 2-(benzyloxyimino)-ethoxy | OCH₃ | H | phenyl | CH | |
| 1.067 | 2-(3-chloroallyloxyimino)-phenoxy | OCH₃ | H | phenyl | CH | |
| 1.068 | 2-(ethoxyimino)propyloxy | OCH₃ | H | phenyl | CH | |
| 1.069 | H | OCH₃ | H | phenyl | CH | |
| 1.070 | benzyloxy | OCH₃ | H | phenyl | CH | |
| 1.071 | propargyloxy | OCH₃ | H | phenyl | CH | |
| 1.072 | allyloxy | OCH₃ | H | phenyl | CH | |
| 1.073 | methoxymethoxy | OCH₃ | H | phenyl | CH | |
| 1.074 | 2-trifluoroethoxy | OCH₃ | H | phenyl | CH | |
| 1.075 | phenoxy | OCH₃ | H | phenyl | CH | |
| 1.076 | 3-dichloroallyloxy | OCH₃ | H | phenyl | CH | |
| 1.077 | 1-phenylethan-1-iminoxy | OCH₃ | H | phenyl | CH | |
| 1.078 | OH | CF₃ | H | phenyl | CH | 103-107 |
| 1.079 | OH | OCHF₂ | H | phenyl | CH | |
| 1.080 | OK | OCH₃ | H | phenyl | CH | 248-250 |
| 1.081 | ONa | OCH₃ | H | phenyl | CH | 197-210 |
| 1.082 | OH | SCH₃ | H | phenyl | N | |
| 1.083 | cyclohexyloxy | OCH₃ | H | phenyl | CH | |
| 1.084 | cyclopentyloxy | OCH₃ | H | phenyl | CH | |
| 1.085 | OCH₂COOC₂H₅ | OCH₃ | H | phenyl | CH | |
| 1.086 | 2-(phenoxy)-ethoxy | OCH₃ | H | phenyl | CH | |
| 1.087 | phenylcarbonylmethoxy | OCH₃ | H | phenyl | CH | |
| 1.088 | 4,5-dichloroimidazol-1-yl | OCH₃ | H | phenyl | CH | |
| 1.089 | pyrazol-1-yl | OCH₃ | H | phenyl | CH | |
| 1.090 | OH | OCH₃ | CH₃ | phenyl | CH | 77-81 |
| 1.091 | 2-(4-methoxyphenoxy)-ethoxy | OCH₃ | H | phenyl | CH | |
| 1.092 | OH | OCH₃ | H | 4-ethoxycarbonylphenyl | CH | |
| 1.093 | OCH₃ | OCH₃ | H | 4-fluorophenyl | CH | 166-168 |
| 1.094 | OCH₃ | OCH₃ | H | 4-methoxyphenyl | CH | 112-121 |
| 1.095 | OCH₃ | OCH₃ | H | 3,5-dichlorophenyl | CH | 130-139 |
| 1.096 | OCH₃ | OCH₃ | H | 4-chlorophenyl | CH | 149-150 |
| 1.097 | OCH₃ | OCH₃ | H | 2-fluorophenyl | CH | 111-114 |
| 1.098 | OCH₃ | OCH₃ | H | 3-methylphenyl | CH | 70-80 |
| 1.099 | OCH₃ | OCH₃ | H | 4-methylphenyl | CH | 98-103 |
| 1.100 | OCH₃ | OCH₃ | H | 4-nitrophenyl | CH | 124-135 |
| 1.101 | OCH₃ | OCH₃ | H | 3-methoxyphenyl | CH | 73-112 |
| 1.102 | OH | CF₃ | H | 4-methoxyphenyl | CH | 152-155 |
| 1.103 | OH | CF₃ | H | 4-chlorophenyl | CH | 163-170 |
| 1.104 | O⁻mor⁺ᵃ⁾ | OCH₃ | H | 4-chlorophenyl | CH | 148-149 |
| 1.105 | OH | OCH₃ | H | 4-nitrophenyl | CH | 144-151 |
| 1.106 | OH | OCH₃ | H | 4-phenoxyphenyl | CH | 67-78 |
| 1.107 | OH | OCH₃ | H | 3-methoxyphenyl | CH | 144-150 |

TABLE 1-continued

Compounds I in which A is substituted or unsubstituted phenyl

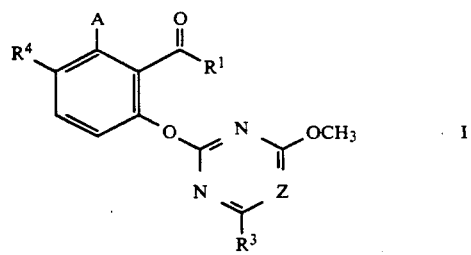

| No. | R¹ | R³ | R⁴ | A | Z | Phys. data mp. [°C.] |
|---|---|---|---|---|---|---|
| 1.108 | OH | OCH₃ | H | 4-carboxyphenyl | CH | 135–137 |
| 1.109 | OH | OCH₃ | H | 4-trifluoromethylphenyl | N | 138–144 |
| 1.110 | OC₂H₅ | OCH₃ | H | phenyl | CH | 119–130 |
| 1.111 | OH | OCH₃ | H | 4-(4-fluorophenoxy)phenyl | CH | 50–56 |
| 1.112 | OH | OCH₃ | H | 4-phenylphenyl | CH | 142–143 |
| 1.113 | OH | OCH₃ | H | 2-nitrophenyl | CH | 156–160 |
| 1.114 | O⁻mor⁺ ᵃ⁾ | OCH₃ | H | phenyl | CH | 166–168 |
| 1.115 | O⁻atr⁺ ᵇ⁾ | OCH₃ | H | phenyl | CH | 99–105 |
| 1.116 | O⁻NH₄⁺ | OCH₃ | H | phenyl | CH | 160–164 |
| 1.117 | O⁻Li⁺ | OCH₃ | H | phenyl | CH | 215–217 |
| 1.118 | O⁻(0.5Ca²⁺) | OCH₃ | H | phenyl | CH | 209–210 |
| 1.119 | O⁻N(C₄H₉)₄⁺ | OCH₃ | H | phenyl | CH | resin |

ᵃ⁾mor⁻ = morpholinyl ion
ᵇ⁾atr⁺ = aminotriazolyl ion

TABLE 2

Compounds I in which A is a heterocyclic or bicyclic radical

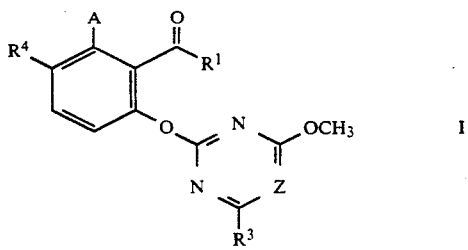

| No. | R¹ | R³ | R⁴ | A | Z | Phys. data mp. [°C.] |
|---|---|---|---|---|---|---|
| 2.001 | OH | CH₃ | H | pyrazol-1-yl | N | |
| 2.002 | OH | OCH₃ | H | pyrazol-1-yl | N | |
| 2.003 | OH | OCH₃ | H | pyrazol-1-yl | CH | 120–125, decomp. |
| 2.004 | OC₂H₅ | OCH₃ | H | pyrazol-1-yl | CH | 94–96 |
| 2.005 | OC₂H₅ | OCH₃ | H | 4-methylpyrazol-1-yl | CH | |
| 2.006 | OC₂H₅ | OCH₃ | H | 3,5-dimethylpyrazol-1-yl | CH | |
| 2.007 | OH | OCH₃ | H | 3,5-dimethylpyrazol-1-yl | CH | 149–152 |
| 2.008 | OH | OCH₃ | H | 3(5)-methylpyrazol-1-yl | CH | 158–160 |
| 2.009 | OH | OCH₃ | H | 4-methylpyrazol-1-yl | CH | 154–157 |
| 2.010 | OC₂H₅ | OCH₃ | H | 4-chloropyrazol-1-yl | CH | |
| 2.011 | OH | OCH₃ | H | 4-chloropyrazol-1-yl | CH | 134–138 |
| 2.012 | OH | OCH₃ | H | 4-bromopyrazol-1-yl | CH | |
| 2.013 | OH | OCH₃ | H | 4-phenylpyrazol-1-yl | CH | 156–158 |
| 2.014 | OC₂H₅ | OCH₃ | H | 4-phenylpyrazol-1-yl | CH | |
| 2.015 | OH | OCH₃ | H | 3,4,5-trimethylpyrazol-1-yl | CH | 142–150 |
| 2.016 | OH | OCH₃ | H | 4-chloro-3,5-dimethylpyrazol-1-yl | CH | 71–76 |
| 2.017 | OH | OCH₃ | H | 4-isopropylpyrazol-1-yl | CH | |
| 2.018 | OH | OCH₃ | H | 3(5)-phenylpyrazol-1-yl | CH | 100 (Z) |
| 2.019 | OH | OCH₃ | H | 3(5)-methyl-5(3)-phenylpyrazol-1-yl | CH | 132 (Z) |
| 2.020 | OH | OCH₃ | H | 3,5-bistrifluormethylpyrazol-1-yl | CH | |
| 2.021 | OH | OCH₃ | H | 4-nitropyrazol-1-yl | CH | |
| 2.022 | methylthiomethoxy | OCH₃ | H | pyrazol-1-yl | CH | 88–91 |
| 2.023 | methoxyethoxy | OCH₃ | H | pyrazol-1-yl | CH | |
| 2.024 | OCH₂—co—OC₂H₅ | OCH₃ | H | pyrazol-1-yl | CH | oil |
| 2.025 | OH | OCH₃ | H | imidazolyl-1-yl | CH | 199–201 |
| 2.026 | OH | OCH₃ | H | 2-methylimidazol-1-yl | CH | |
| 2.027 | OH | OCH₃ | H | 4,5-dimethylimidazol-1-yl | CH | |
| 2.028 | OH | OCH₃ | H | 2-phenylimidazol-1-yl | CH | 164–165 |
| 2.029 | OH | OCH₃ | H | 4,5-dichloroimidazol-1-yl | CH | |
| 2.030 | OH | OCH₃ | H | 2,4,5-trichloroimidazol-1-yl | CH | |
| 2.031 | OH | OCH₃ | H | 2-methyl-4,5-dichloroimidazol-1-yl | CH | |
| 2.032 | OH | OCH₃ | H | 2-methyl-4,5-dibromoimidazol-1-yl | CH | |

TABLE 2-continued

Compounds I in which A is a heterocyclic or bicyclic radical

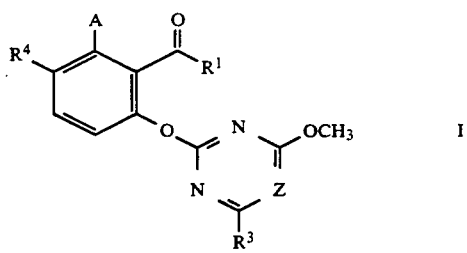

| No. | R¹ | R³ | R⁴ | A | Z | Phys. data mp. [°C.] |
|---|---|---|---|---|---|---|
| 2.033 | OH | OCH₃ | H | 4(5)-chloro-5(4)-methylimidazol-1-yl | CH | |
| 2.034 | OH | OCH₃ | H | 4(5)-nitroimidazol-yl | CH | |
| 2.035 | OH | OCH₃ | H | [1,2,4]-triazol-1-yl | CH | 158–160 |
| 2.036 | OH | OCH₃ | H | 3(5)-methyl-[1,2,4]-triazol-1-yl | CH | 166–168 |
| 2.037 | OH | OCH₃ | H | 3(5)-phenyl-[1,2,4]-triazol-1-yl | CH | 135–140 |
| 2.038 | OH | OCH₃ | H | 3,5-dimethyl-[1,2,4]-triazol-1-yl | CH | 187–189 |
| 2.039 | OH | OCH₃ | H | [1,2,3]-triazol-1-yl | CH | |
| 2.040 | OH | OCH₃ | H | 4,5-dimethyl-[1,2,3]-triazol-1-yl | CH | |
| 2.041 | OH | OCH₃ | H | 4(5)-phenyl-[1,2,3]-triazol-1-yl | CH | |
| 2.042 | OH | OCH₃ | H | [1,2,3,4]-tetrazol-1-yl | CH | |
| 2.043 | OC₂H₅ | OCH₃ | H | 1-methylpyrazol-4-yl | CH | |
| 2.044 | OC₂H₅ | OCH₃ | H | 1-phenylpyrazol-4-yl | CH | |
| 2.045 | OH | OCH₃ | H | 1-phenylpyrazol-4-yl | CH | |
| 2.046 | OC₂H₅ | OCH₃ | H | 1,3,5-trimethylpyrazol-4-yl | CH | |
| 2.047 | OH | OCH₃ | H | 1,3,5-trimethylpyrazol-4-yl | CH | |
| 2.048 | OH | OCH₃ | H | 1-methylpyrazol-4-yl | CH | |
| 2.049 | OH | OCH₃ | H | 1-methylpyrazol-5-yl | CH | |
| 2.050 | OH | OCH₃ | H | 1-phenylpyrazol-5-yl | CH | |
| 2.051 | OH | OCH₃ | H | 1-methylpyrazol-3-yl | CH | |
| 2.052 | OH | OCH₃ | H | 1-phenylpyrazol-3-yl | CH | |
| 2.053 | OC₂H₅ | OCH₃ | H | 1-methylpyrazol-3-yl | CH | |
| 2.054 | OH | OCH₃ | H | 1,4-dimethylpyrazol-3-yl | CH | |
| 2.055 | OH | OCH₃ | H | 5-methyl-1-phenylpyrazol-3-yl | CH | |
| 2.056 | OH | OCH₃ | H | 1,5-dimethylpyrazol-3-yl | CH | |
| 2.057 | OH | OCH₃ | H | 1,3-dimethylpyrazol-4-yl | CH | |
| 2.058 | OH | OCH₃ | H | 1,5-dimethylpyrazol-4-yl | CH | |
| 2.059 | OH | OCH₃ | H | 3-methyl-1-phenylpyrazol-4-yl | CH | |
| 2.060 | OH | OCH₃ | H | 5-methyl-1-phenylpyrazol-4-yl | CH | |
| 2.061 | OH | OCH₃ | H | 3,5-dimethyl-1-phenylpyrazol-4-yl | CH | |
| 2.062 | OH | OCH₃ | H | 3-methyl-1-phenylpyrazol-5-yl | CH | |
| 2.063 | OH | OCH₃ | H | 1,4-dimethylpyrazol-5-yl | CH | |
| 2.064 | OH | OCH₃ | H | 1,3-dimethylpyrazol-5-yl | CH | |
| 2.065 | OH | OCH₃ | H | 1-methyl-[1,2,3]-triazol-5-yl | CH | |
| 2.066 | OH | OCH₃ | H | 1-phenyl-[1,2,3]-triazol-5-yl | CH | |
| 2.067 | OH | OCH₃ | H | 1-phenyl-[1,2,3]-triazol-4-yl | CH | |
| 2.068 | OH | OCH₃ | H | 5-methyl-1-phenyl-[1,2,3]-triazol-4-yl | CH | |
| 2.069 | OH | OCH₃ | H | 5-methyl-1-phenyl-[1,2,4]-triazol-3-yl | CH | |
| 2.070 | OC₂H₅ | OCH₃ | H | 1-methylimidazol-2-yl | CH | |
| 2.071 | OH | OCH₃ | H | 1-methylimidazol-2-yl | CH | |
| 2.072 | OH | OCH₃ | H | 1,4-dimethylimidazol-5-yl | CH | |
| 2.073 | OH | OCH₃ | H | 1-methyl-5-nitroimidazol-2-yl | CH | |
| 2.074 | OH | OCH₃ | H | 1-methylimidazol-5-yl | CH | |
| 2.075 | OH | OCH₃ | H | 1-phenylimidazol-5-yl | CH | |
| 2.076 | OH | OCH₃ | H | 2-thienyl | CH | 70–75 |
| 2.077 | OH | OCH₃ | H | 3-thienyl | CH | |
| 2.078 | OH | OCH₃ | H | 2,3-dichloro-4-thienyl | CH | |
| 2.079 | OH | OCH₃ | H | 2,5-dichloro-3-thienyl | CH | |
| 2.080 | OH | OCH₃ | H | 2-bromo-5-thienyl | CH | |
| 2.081 | OH | OCH₃ | H | 4-bromo-2-thienyl | CH | |
| 2.082 | OH | OCH₃ | H | 3-methyl-2-thienyl | CH | |
| 2.083 | OH | OCH₃ | H | 2-chloro-5-thienyl | CH | |
| 2.084 | OH | OCH₃ | H | 2-methyl-5-thienyl | CH | |
| 2.085 | OH | OCH₃ | H | 2-nitro-5-thienyl | CH | |
| 2.086 | 1-imidazolyl | OCH₃ | H | 2-thienyl | CH | |
| 2.087 | 2-propaniminoxy | OCH₃ | H | 3-thienyl | CH | |
| 2.088 | methylthiomethoxy | OCH₃ | H | 2-thienyl | CH | |
| 2.089 | ethoxycarbonylmethoxy | OCH₃ | H | 3-thienyl | CH | |
| 2.090 | allyloxy | OCH₃ | H | 2-chloro-5-thienyl | CH | |
| 2.091 | propargyloxy | OCH₃ | H | 2-methyl-5-thienyl | CH | |
| 2.092 | OH | OCH₃ | H | isoxazol-5-yl | CH | |
| 2.093 | OH | OCH₃ | H | 3-methylisoxazol-5-yl | CH | |
| 2.094 | OH | OCH₃ | H | 3-isopropylisoxazol-5-yl | CH | |
| 2.095 | OH | OCH₃ | H | 3-phenylisoxazol-5-yl | CH | |
| 2.096 | OH | OCH₃ | H | 3-methyl-4-chloroisoxazol-5-yl | CH | |
| 2.097 | OH | OCH₃ | H | 3-methylisoxazol-4-yl | CH | |
| 2.098 | OH | OCH₃ | H | isoxazol-4-yl | CH | |

TABLE 2-continued

Compounds I in which A is a heterocyclic or bicyclic radical

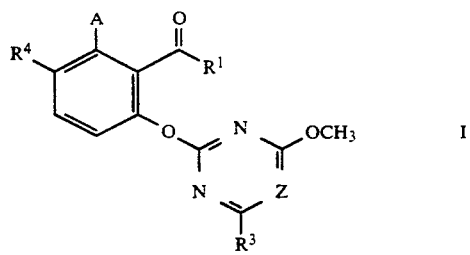

| No. | R$^1$ | R$^3$ | R$^4$ | A | Z | Phys. data mp. [°C.] |
|---|---|---|---|---|---|---|
| 2.099 | OH | OCH$_3$ | H | 3,5-dimethylisoxazol-4-yl | CH | |
| 2.100 | OC$_2$H$_5$ | OCH$_3$ | H | 3-isopropylisoxazol-5-yl | CH | |
| 2.101 | benzyloxy | OCH$_3$ | H | 3-isopropylisoxazol-5-yl | CH | |
| 2.102 | OH | OCH$_3$ | H | 2-methyloxazol-4-yl | CH | |
| 2.103 | OH | OCH$_3$ | H | oxazol-2-yl | CH | |
| 2.104 | OH | OCH$_3$ | H | 2-methylthiazol-4-yl | CH | |
| 2.105 | OH | OCH$_3$ | H | 3-isopropylisoxazol-5-yl | CH | |
| 2.106 | OH | OCH$_3$ | H | thiazol-4-yl | CH | |
| 2.107 | OH | OCH$_3$ | H | 2-benzylthiazol-4-yl | CH | |
| 2.108 | OH | OCH$_3$ | H | 5-chloro-2-phenylthiazol-4-yl | CH | |
| 2.109 | OH | OCH$_3$ | H | thiazol-2-yl | CH | |
| 2.110 | OH | OCH$_3$ | H | thiazol-5-yl | CH | |
| 2.111 | OH | OCH$_3$ | H | 4-methylthiazol-2-yl | CH | |
| 2.112 | OH | OCH$_3$ | H | 5-methylthiazol-2-yl | CH | |
| 2.113 | OH | OCH$_3$ | H | 4-phenylthiazol-2-yl | CH | |
| 2.114 | OH | OCH$_3$ | H | 4-methylthiazol-5-yl | CH | |
| 2.115 | OH | OCH$_3$ | H | 2-methylthiazol-5-yl | CH | |
| 2.116 | OH | OCH$_3$ | H | 2-phenylthiazol-5-yl | CH | |
| 2.117 | OC$_2$H$_5$ | OCH$_3$ | H | 2-phenylthiazol-5-yl | CH | |
| 2.118 | OH | OCH$_3$ | H | [1,3,4]thiadiazol-2-yl | CH | |
| 2.119 | OH | OCH$_3$ | H | 5-methyl-[1,3,4]thiadiazol-2-yl | CH | |
| 2.120 | OH | OCH$_3$ | H | 5-phenyl-[1,3,4]thiadiazol-2-yl | CH | |
| 2.121 | OH | OCH$_3$ | H | 2-pyridyl | CH | |
| 2.122 | OH | OCH$_3$ | H | 3-pyridyl | CH | |
| 2.123 | OH | OCH$_3$ | H | 4-pyridyl | CH | |
| 2.124 | OH | OCH$_3$ | H | 6-methyl-2-pyridyl | CH | |
| 2.125 | OH | OCH$_3$ | H | 3-chloro-5-pyridyl | CH | |
| 2.126 | OH | OCH$_3$ | H | 5-chloro-2-pyridyl | CH | |
| 2.127 | OH | OCH$_3$ | H | quinolin-2-yl | CH | |
| 2.128 | OH | OCH$_3$ | H | quinolin-4-yl | CH | |
| 2.129 | OH | OCH$_3$ | H | quinolin-8-yl | CH | |
| 2.130 | OH | OCH$_3$ | H | 7-chloroquinolin-8-yl | CH | |
| 2.131 | OH | OCH$_3$ | H | 7-chloro-3-methylquinolin-8-yl | CH | |
| 2.132 | OH | OCH$_3$ | H | 3,7-dichloroquinolin-8-yl | CH | |
| 2.133 | OH | OCH$_3$ | H | 1-naphthyl | CH | |
| 2.134 | OH | OCH$_3$ | H | 2-naphthyl | CH | 132–138 |
| 2.135 | OH | OCH$_3$ | H | 2-methyl-1-naphthyl | CH | |
| 2.136 | OH | OCH$_3$ | H | 2-methoxy-1-naphthyl | CH | |
| 2.137 | OH | OCH$_3$ | H | 1-chloro-4-naphthyl | CH | |
| 2.138 | OC$_2$H$_5$ | OCH$_3$ | H | 2-naphthyl | CH | |
| 2.139 | OC$_2$H$_4$SC$_2$H$_5$ | OCH$_3$ | H | 2-naphthyl | CH | |
| 2.140 | OC$_2$H$_5$ | OCH$_3$ | H | 2-pyridyl | CH | |
| 2.141 | allyloxy | OCH$_3$ | H | 3-pyridyl | CH | |
| 2.142 | OCH$_3$ | OCH$_3$ | H | pyrazol-1-yl | CH | |
| 2.143 | 2-propaniminoxy | OCH$_3$ | H | pyrazol-1-yl | CH | 117–120 |
| 2.144 | OCH$_3$ | OCH$_3$ | H | indazol-1-yl | CH | |
| 2.145 | OCH$_3$ | OCH$_3$ | H | benztriazol-1-yl | CH | |
| 2.146 | OCH$_3$ | OCH$_3$ | H | 3,5-dimethylpyrazol-1-yl | CH | |
| 2.147 | OCH$_3$ | OCH$_3$ | H | 3(5)-methylpyrazol-1-yl | CH | |
| 2.148 | OCH$_3$ | OCH$_3$ | H | 4-methylpyrazol-1-yl | CH | |
| 2.149 | OCH$_3$ | OCH$_3$ | H | 4-chloropyrazol-1-yl | CH | |
| 2.150 | OCH$_3$ | OCH$_3$ | H | 4-bromopyrazol-1-yl | CH | |
| 2.151 | OCH$_3$ | OCH$_3$ | H | 4-phenylpyrazol-1-yl | CH | |
| 2.152 | OCH$_3$ | OCH$_3$ | H | 3,4,5-trimethylpyrazol-1-yl | CH | |
| 2.153 | OCH$_3$ | OCH$_3$ | H | 4-chloro-3,5-dimethylpyrazol-1-yl | CH | |
| 2.154 | OCH$_3$ | OCH$_3$ | H | 4-isopropylpyrazol-1-yl | CH | |
| 2.155 | OCH$_3$ | OCH$_3$ | H | 3(5)-phenylpyrazol-1-yl | CH | |
| 2.156 | OCH$_3$ | OCH$_3$ | H | 3(5)-methyl-5(3)-phenylpyrazol-1-yl | CH | |
| 2.157 | OCH$_3$ | OCH$_3$ | H | 3,5-bistrifluoromethylpyrazol-1-yl | CH | |
| 2.158 | OCH$_3$ | OCH$_3$ | H | 4-nitropyrazol-1-yl | CH | |
| 2.159 | OCH$_3$ | OCH$_3$ | H | imidazol-1-yl | CH | |
| 2.160 | OCH$_3$ | OCH$_3$ | H | 2-methylimidazol-1-yl | CH | |
| 2.161 | OCH$_3$ | OCH$_3$ | H | 4,5-dimethylimidazol-1-yl | CH | |
| 2.162 | OCH$_3$ | OCH$_3$ | H | 2-phenylimidazol-1-yl | CH | |
| 2.163 | OCH$_3$ | OCH$_3$ | H | 4,5-dichloroimidazol-1-yl | CH | |
| 2.164 | OCH$_3$ | OCH$_3$ | H | 2,4,5-trichloroimidazol-1-yl | CH | |

TABLE 2-continued

Compounds I in which A is a heterocyclic or bicyclic radical

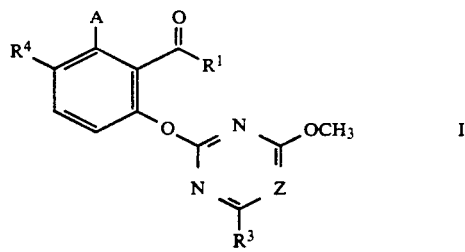

| No. | R¹ | R³ | R⁴ | A | Z | Phys. data mp. [°C.] |
|---|---|---|---|---|---|---|
| 2.165 | OCH₃ | OCH₃ | H | 2-methyl-4,5-dichloroimidazol-1-yl | CH | |
| 2.166 | OCH₃ | OCH₃ | H | 2-methyl-4,5-dibromoimidazol-1-yl | CH | |
| 2.167 | OCH₃ | OCH₃ | H | 4(5)-chloro-5(4)methylimidazol-1-yl | CH | |
| 2.168 | OCH₃ | OCH₃ | H | 4(5)-nitroimidazol-1-yl | CH | |
| 2.169 | OCH₃ | OCH₃ | H | [1,2,4]-triazol-1-yl | CH | |
| 2.170 | OCH₃ | OCH₃ | H | 3(5)-methyl-[1,2,4]-triazol-1-yl | CH | |
| 2.171 | OCH₃ | OCH₃ | H | 3(5)-phenyl-[1,2,4]-triazol-1-yl | CH | |
| 2.172 | OCH₃ | OCH₃ | H | 3,5-dimethyl-[1,2,4]-triazol-1-yl | CH | |
| 2.173 | OCH₃ | OCH₃ | H | [1,2,3]-triazol-1-yl | CH | |
| 2.174 | OCH₃ | OCH₃ | H | 4,5-dimethyl-[1,2,3]-triazol-1-yl | CH | |
| 2.175 | OCH₃ | OCH₃ | H | 4(5)-phenyl-[1,2,3]-triazol-1-yl | CH | |
| 2.176 | OCH₃ | OCH₃ | H | [1,2,3,4]-tetrazol-1-yl | CH | |
| 2.177 | OCH₃ | OCH₃ | H | 1-phenylpyrazol-4-yl | CH | |
| 2.178 | OCH₃ | OCH₃ | H | 1,3,5-trimethylpyrazol-4-yl | CH | |
| 2.179 | OCH₃ | OCH₃ | H | 1-methylpyrazol-4-yl | CH | |
| 2.180 | OCH₃ | OCH₃ | H | 1-methylpyrazol-5-yl | CH | |
| 2.181 | OCH₃ | OCH₃ | H | 1-phenylpyrazol-5-yl | CH | |
| 2.182 | OCH₃ | OCH₃ | H | 1-methylpyrazol-3-yl | CH | |
| 2.183 | OCH₃ | OCH₃ | H | 1-Phenylpyrazol-3-yl | CH | |
| 2.184 | OCH₃ | OCH₃ | H | 1,4-dimethylpyrazol-3-yl | CH | |
| 2.185 | OCH₃ | OCH₃ | H | 5-methyl-1-phenylpyrazol-3-yl | CH | |
| 2.186 | OCH₃ | OCH₃ | H | 1,5-dimethylpyrazol-3-yl | CH | |
| 2.187 | OCH₃ | OCH₃ | H | 1,3-dimethylpyrazol-4-yl | CH | |
| 2.188 | OCH₃ | OCH₃ | H | 1,5-dimethylpyrazol-4-yl | CH | |
| 2.189 | OCH₃ | OCH₃ | H | 3-methyl-1-phenylpyrazol-4-yl | CH | |
| 2.190 | OCH₃ | OCH₃ | H | 5-methyl-1-phenylpyrazol-4-yl | CH | |
| 2.191 | OCH₃ | OCH₃ | H | 3,5-dimethyl-1-phenylpyrazol-4-yl | CH | |
| 2.192 | OCH₃ | OCH₃ | H | 3-methyl-1-phenylpyrazol-5-yl | CH | |
| 2.193 | OCH₃ | OCH₃ | H | 1,4-dimethylpyrazol-5-yl | CH | |
| 2.194 | OCH₃ | OCH₃ | H | 1,3-dimethylpyrazol-5-yl | CH | |
| 2.195 | OCH₃ | OCH₃ | H | 1-methyl-[1,2,3]-triazol-5-yl | CH | |
| 2.196 | OCH₃ | OCH₃ | H | 1-phenyl-[1,2,3]-triazol-5-yl | CH | |
| 2.197 | OCH₃ | OCH₃ | H | 1-phenyl-[1,2,3]-triazol-4-yl | CH | |
| 2.198 | OCH₃ | OCH₃ | H | 5-methyl-1-phenyl-[1,2,3]-triazol-4-yl | CH | |
| 2.199 | OCH₃ | OCH₃ | H | 5-methyl-1-phenyl-[1,2,4]-triazol-3-yl | CH | |
| 2.200 | OCH₃ | OCH₃ | H | 1-methylimidazol-2-yl | CH | |
| 2.201 | OCH₃ | OCH₃ | H | 1,4-dimethylimidazol-5-yl | CH | |
| 2.202 | OCH₃ | OCH₃ | H | 1-methyl-5-nitroimidazol-2-yl | CH | |
| 2.203 | OCH₃ | OCH₃ | H | 1-methylimidazol-5-yl | CH | |
| 2.204 | OCH₃ | OCH₃ | H | 1-phenylimidazol-5-yl | CH | |
| 2.205 | OCH₃ | OCH₃ | H | 2-thienyl | CH | |
| 2.206 | OCH₃ | OCH₃ | H | 3-thienyl | CH | |
| 2.207 | OCH₃ | OCH₃ | H | 2,3-dichloro-4-thienyl | CH | |
| 2.208 | OCH₃ | OCH₃ | H | 2,5-dichloro-3-thienyl | CH | |
| 2.209 | OCH₃ | OCH₃ | H | 2-bromo-5-thienyl | CH | |
| 2.210 | OCH₃ | OCH₃ | H | 4-bromo-2-thienyl | CH | |
| 2.211 | OCH₃ | OCH₃ | H | 3-methyl-2-thienyl | CH | |
| 2.212 | OCH₃ | OCH₃ | H | 2-chloro-5-thienyl | CH | |
| 2.213 | OCH₃ | OCH₃ | H | 2-methyl-5-thienyl | CH | |
| 2.214 | OCH₃ | OCH₃ | H | 2-nitro-5-thienyl | CH | |
| 2.215 | OCH₃ | OCH₃ | H | isoxazol-5-yl | CH | |
| 2.216 | OCH₃ | OCH₃ | H | 3-methylisoxazol-5-yl | CH | |
| 2.217 | OCH₃ | OCH₃ | H | 3-isopropylisoxazol-5-yl | CH | |
| 2.218 | OCH₃ | OCH₃ | H | 3-phenylisoxazol-5-yl | CH | |
| 2.219 | OCH₃ | OCH₃ | H | 3-methyl-4-chlorisoxazol-5-yl | CH | |
| 2.220 | OCH₃ | OCH₃ | H | 3-methylisoxazol-4-yl | CH | |
| 2.221 | OCH₃ | OCH₃ | H | isoxazol-4-yl | CH | |
| 2.222 | OCH₃ | OCH₃ | H | 3,5-dimethylisoxazol-4-yl | CH | |
| 2.223 | OCH₃ | OCH₃ | H | 2-methyloxazol-4-yl | CH | |
| 2.224 | OCH₃ | OCH₃ | H | oxazol-2-yl | CH | |
| 2.225 | OCH₃ | OCH₃ | H | 2-methylthiazol-4-yl | CH | |
| 2.226 | OCH₃ | OCH₃ | H | 2-phenylthiazol-4-yl | CH | |
| 2.227 | OCH₃ | OCH₃ | H | thiazol-4-yl | CH | |
| 2.228 | OCH₃ | OCH₃ | H | 2-benzylthiazol-4-yl | CH | |
| 2.229 | OCH₃ | OCH₃ | H | 5-chloro-2-phenylthiazol-4-yl | CH | |
| 2.230 | OCH₃ | OCH₃ | H | thiazol-2-yl | CH | |

TABLE 2-continued

Compounds I in which A is a heterocyclic or bicyclic radical

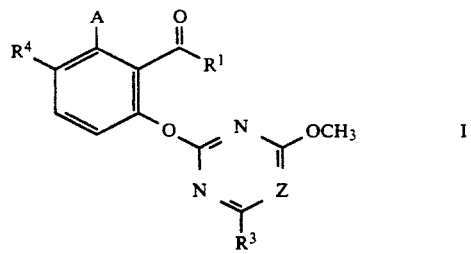

| No. | R¹ | R³ | R⁴ | A | Z | Phys. data mp. [°C.] |
|---|---|---|---|---|---|---|
| 2.231 | OCH₃ | OCH₃ | H | thiazol-5-yl | CH | |
| 2.232 | OCH₃ | OCH₃ | H | 4-methylthiazol-2-yl | CH | |
| 2.233 | OCH₃ | OCH₃ | H | 5-methylthiazol-2-yl | CH | |
| 2.234 | OCH₃ | OCH₃ | H | 4-phenylthiazol-2-yl | CH | |
| 2.235 | OCH₃ | OCH₃ | H | 4-methylthiazol-5-yl | CH | |
| 2.236 | OCH₃ | OCH₃ | H | 2-methylthiazol-5-yl | CH | |
| 2.237 | OCH₃ | OCH₃ | H | 2-phenylthiazol-5-yl | CH | |
| 2.238 | OCH₃ | OCH₃ | H | [1,3,4]thiadiazol-2-yl | CH | |
| 2.239 | OCH₃ | OCH₃ | H | 5-methyl[1,3,4]thiadiazol-2-yl | CH | |
| 2.240 | OCH₃ | OCH₃ | H | 5-phenyl[1,3,4]thiadiazol-2-yl | CH | |
| 2.241 | OCH₃ | OCH₃ | H | 2-pyridyl | CH | |
| 2.242 | OCH₃ | OCH₃ | H | 3-pyridyl | CH | |
| 2.243 | OCH₃ | OCH₃ | H | 4-pyridyl | CH | |
| 2.244 | OCH₃ | OCH₃ | H | 6-methyl-2-pyridyl | CH | |
| 2.245 | OCH₃ | OCH₃ | H | 3-chloro-5-pyridyl | CH | |
| 2.246 | OCH₃ | OCH₃ | H | 5-chloro-2-pyridyl | CH | |
| 2.247 | OCH₃ | OCH₃ | H | quinolin-2-yl | CH | |
| 2.248 | OCH₃ | OCH₃ | H | quinolin-4-yl | CH | |
| 2.249 | OCH₃ | OCH₃ | H | quinolin-8-yl | CH | |
| 2.250 | OCH₃ | OCH₃ | H | 7-chloroquinolin-8-yl | CH | |
| 2.251 | OCH₃ | OCH₃ | H | 7-chloro-3-methylquinolin-8-yl | CH | |
| 2.252 | OCH₃ | OCH₃ | H | 3,7-dichloroquinolin-8-yl | CH | |
| 2.253 | OCH₃ | OCH₃ | H | 1-naphthyl | CH | |
| 2.254 | OCH₃ | OCH₃ | H | 2-naphthyl | CH | |
| 2.255 | OCH₃ | OCH₃ | H | 2-methyl-1-naphthyl | CH | |
| 2.256 | OCH₃ | OCH₃ | H | 2-methoxy-1-naphthyl | CH | |
| 2.257 | OCH₃ | OCH₃ | H | 1-chloro-4-naphthyl | CH | |
| 2.258 | OH | OCH₃ | H | 3-isopropylpyrazol-1-yl | CH | 55-60 |
| 2.259 | OH | OCH₃ | H | 3-t.butylpyrazol-1-yl | CH | 80 (Z) |
| 2.260 | OC₂H₅ | OCH₃ | H | imidazol-1-yl | CH | oil |
| 2.261 | OC₂H₅ | OCH₃ | H | 1,2,4-triazol-1-yl | CH | oil |
| 2.262 | OH | OCH₃ | H | indazol-1-yl | CH | 95-100 |
| 2.263 | OH | OCH₃ | H | 3-n-propylpyrazol-1-yl | CH | 48-50 |
| 2.264 | OH | OCH₃ | H | 3-isobutylpyrazol-1-yl | CH | 88-90 |
| 2.265 | OH | OCH₃ | H | 3-neopentylpyrazol-1-yl | CH | 52-55 |
| 2.266 | OH | OCH₃ | H | 3-thiomethyl-1,2,4-triazol-1-yl | CH | 158-60 |
| 2.267 | OH | OCH₃ | H | 3-thiomethyl-5-methyl-1,2,4-triazol-1-yl | CH | 159-61 |
| 2.268 | OH | OCH₃ | H | 3-phenyl-5-methyl-1,2,4-triazol-1-yl | CH | 115-120 |

TABLE 3

Salicylic acid derivatives of the formula II'

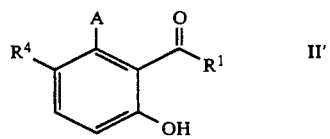

| No. | R¹ | R⁴ | A | Phys. data mp. [°C.] |
|---|---|---|---|---|
| 3.001 | OH | H | 2-fluorophenyl | |
| 3.002 | OH | H | 4-fluorophenyl | 250-255 (decomp.)ᵃ |
| 3.003 | OH | H | 2,6-difluorophenyl | |
| 3.004 | OH | H | 2,4-difluorophenyl | |
| 3.005 | OH | H | 2-fluoro-4-trifluoromethylphenyl | |
| 3.006 | OH | H | 2-chlorophenyl | 168-179 |
| 3.007 | OH | H | 2-bromophenyl | |
| 3.008 | OH | H | 2-chloro-6-fluorophenyl | |
| 3.009 | OH | H | pentafluorophenyl | |
| 3.010 | OH | H | 2,4-dichlorophenyl | |
| 3.011 | OH | H | 2,6-dichlorophenyl | |
| 3.012 | OH | H | 2-chloro-4-fluorophenyl | |

TABLE 3-continued

Salicylic acid derivatives of the formula II'

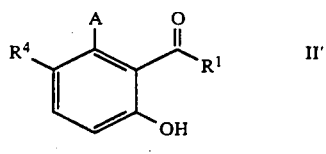

| No. | R¹ | R⁴ | A | |
|---|---|---|---|---|
| 3.013 | OH | H | 3,5-dichlorophenyl | |
| 3.014 | OH | H | 2-methylphenyl | 140–143 |
| 3.015 | OH | H | 2-chloro-6-methylphenyl | |
| 3.016 | OH | H | 3-methylphenyl | |
| 3.017 | OH | H | 4-methylphenyl | |
| 3.018 | OH | H | 2,6-dimethylphenyl | |
| 3.019 | OH | H | 3,5-dimethylphenyl | |
| 3.020 | OH | H | 2,4,6-trimethylphenyl | 75–78 |
| 3.021 | OH | H | 2,4-dimethylphenyl | |
| 3.022 | OH | H | 2-chloro-4-methylphenyl | |
| 3.023 | OH | H | 2,3,5-trichlorophenyl | |
| 3.024 | OH | H | 4-methoxyphenyl | |
| 3.025 | OH | H | 2-methoxyphenyl | 150–152 |
| 3.026 | OH | H | 4-chloro-2-methoxyphenyl | |
| 3.027 | OH | H | 2-trifluoromethylphenyl | |
| 3.028 | OH | H | 2,3-dimethyl-4-methoxyphenyl | |
| 3.029 | OH | H | 2-dimethylamino-2-methylphenyl | |
| 3.030 | OH | H | 3-cyanophenyl | |
| 3.031 | OH | H | 3-phenoxyphenyl | |
| 3.032 | OH | H | 3-(3-trifluoromethylphenoxy)phenyl | |
| 3.033 | OH | H | 3-trifluoromethylphenyl | |
| 3.034 | OH | H | 3-bromophenyl | |
| 3.035 | OH | H | 3-chlorophenyl | |
| | | | | Phys. data mp. [°C.], bp [°C./mbar] |
| 3.036 | OH | H | 4-bromophenyl | 168–175 |
| 3.037 | OH | H | 4-chlorophenyl | |
| 3.038 | OH | H | 4-trifluoromethylphenyl | |
| 3.039 | OH | H | 3-(3,4-dichlorophenoxy)phenyl | |
| 3.040 | OH | H | 4-methylthiophenyl | |
| 3.041 | OH | H | 4-t.butylphenyl | 210–225 (decomp.)[a] |
| 3.042 | OH | H | phenyl | |
| 3.043 | ONa | H | phenyl | |
| 3.044 | OH | CH₃ | phenyl | 78–82 |
| 3.045 | OH | H | 4-ethoxycarbonylphenyl | |
| 3.046 | OH | H | pyrazol-1-yl | 175–179 |
| 3.047 | OH | H | 3,5-dimethylpyrazol-1-yl | 182 (decomp.) |
| 3.048 | OH | H | 3(5)-methylpyrazol-1-yl | 184 (decomp.) |
| 3.049 | OH | H | 4-methylpyrazol-1-yl | 162 (decomp.) |
| 3.050 | OH | H | 4-chloropyrazol-1-yl | 175 (decomp.) |
| 3.051 | OH | H | 4-bromopyrazol-1-yl | |
| 3.052 | OH | H | 4-phenylpyrazol-1-yl | 200–202 |
| 3.053 | OH | H | 3,4,5-trimethylpyrazol-1-yl | 180 (decomp.) |
| 3.054 | OH | H | 4-chloro-3,5-dimethylpyrazol-1-yl | 209–212 (decomp.) |
| 3.055 | OH | H | 4-isopropylpyrazol-1-yl | |
| 3.056 | OH | H | 3(5)-phenylpyrazol-1-yl | 212 (decomp.) |
| 3.057 | OH | H | 3(5)-methyl-5(3)-phenylpyrazol-1-yl | 230–234 (decomp.) |
| 3.058 | OH | H | 3,5-bistrifluoromethylpyrazol-1-yl | |
| 3.059 | OH | H | 4-nitropyrazol-1-yl | |
| 3.060 | OH | H | imidazol-1-yl | 216 (decomp.) |
| 3.061 | OH | H | 2-methylimidazol-1-yl | |
| 3.062 | OH | H | 4,5-dimethylimidazol-1-yl | |
| 3.063 | OH | H | 2-phenylimidazol-1-yl | |
| 3.064 | OH | H | 4,5-dichloroimidazol-1-yl | 180 (decomp.) |
| 3.065 | OH | H | 2,4,5-trichloroimidazol-1-yl | |
| 3.066 | OH | H | 2-methyl-4,5-dichloroimidazol-1-yl | |
| 3.067 | OH | H | 2-methyl-4,5-dibromoimidazol-1-yl | |
| 3.068 | OH | H | 4(5)-chloro-5(4)-methylimidazol-1-yl | |
| 3.069 | OH | H | 4(5)-nitroimidazol-1-yl | |
| 3.070 | OH | H | [1,2,4]-triazol-1-yl | 214–215 (decomp.) |
| 3.071 | OH | H | 3(5)-methyl-[1,2,4]-triazol-1-yl | 210–211 (decomp.) |
| 3.072 | OH | H | 3(5)-phenyl-[1,2,4]-triazol-1-yl | 225 (decomp.) |
| 3.073 | OH | H | 3,5-dimethyl-[1,2,4]-triazol-1-yl | 255 (decomp.) |
| 3.074 | OH | H | [1,2,4]-triazol-1-yl | |
| 3.075 | OH | H | 4,5-dimethyl-[1,2,3]-triazol-1-yl | |
| 3.076 | OH | H | 4(5)-phenyl-[1,2,3]-triazol-1-yl | |
| 3.077 | OH | H | [1,2,4]-tetrazol-1-yl | |
| 3.078 | OH | H | 1-phenyl-pyrazol-4-yl-pyrazol-4-yl | |
| 3.079 | OH | H | 1,3,5-trimethylpyrazol-4-yl | |
| 3.080 | OH | H | 1-methylpyrazol-4-yl | |
| 3.081 | OH | H | 1-methylpyrazol-5-yl | |
| 3.082 | OH | H | 1-phenylpyrazol-5-yl | |

TABLE 3-continued

Salicylic acid derivatives of the formula II′

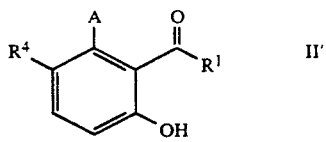

| No. | R¹ | R⁴ | A |
|---|---|---|---|
| 3.083 | OH | H | 1-methylpyrazol-3-yl |
| 3.084 | OH | H | 1-phenylpyrazol-3-yl |
| 3.085 | OH | H | 1,4-dimethylpyrazol-3-yl |
| 3.086 | OH | H | 5-methyl-1-phenyl-pyrazol-3-yl |
| 3.087 | OH | H | 1,5-dimethylpyrazol-3-yl |
| 3.088 | OH | H | 1,3-dimethylpyrazol-4-yl |
| 3.089 | OH | H | 1,5-dimethylpyrazol-4-yl |
| 3.090 | OH | H | 3-methyl-1-phenylpyrazol-4-yl |
| 3.091 | OH | H | 5-methyl-1-phenylpyrazol-4-yl |
| 3.092 | OH | H | 3,5-dimethyl-1-phenylpyrazol-4-yl |
| 3.093 | OH | H | 3-methyl-1-phenylpyrazol-5-yl |
| 3.094 | OH | H | 1,4-dimethylpyrazol-5-yl |
| 3.095 | OH | H | 1,3-dimethylpyrazol-5-yl |
| 3.096 | OH | H | 1-methyl-[1,2,3]-triazol-5-yl |
| 3.097 | OH | H | 1-phenyl-[1,2,4]-triazol-5-yl |
| 3.098 | OH | H | 1-phenyl-[1,2,3]-triazol-4-yl |
| 3.099 | OH | H | 5-methyl-1-phenyl-[1,2,3]-triazol-4-yl |
| 3.100 | OH | H | 5-methyl-1-phenyl-[1,2,4]-triazol-3-yl |
| 3.101 | OH | H | 1-methylimidazol-2-yl |
| 3.102 | OH | H | 1,4-dimethylimidazol-5-yl |
| 3.103 | OH | H | 1-methyl-5-nitroimidazol-2-yl |
| 3.104 | OH | H | 1-methylimidazol-5-yl |
| 3.105 | OH | H | 1-phenylimidazol-5-yl |
| 3.106 | OH | H | 2-thienyl |
| 3.107 | OH | H | 3-thienyl |
| 3.108 | OH | H | 2,3-dichloro-4-thienyl |
| 3.109 | OH | H | 2,5-dichloro-3-thienyl |
| 3.110 | OH | H | 2-bromo-5-thienyl |
| 3.111 | OH | H | 4-bromo-2-thienyl |
| 3.112 | OH | H | 3-methyl-2-thienyl |
| 3.113 | OH | H | 2-chloro-5-thienyl |
| 3.114 | OH | H | 2-methyl-5-thienyl |
| 3.115 | OH | H | 2-nitro-5-thienyl |
| 3.116 | OH | H | isoxazol-5-yl |
| 3.117 | OH | H | 3-methylisoxazol-5-yl |
| 3.118 | OH | H | 3-isopropylisoxazol-5-yl |
| 3.119 | OH | H | 3-phenylisoxazol-5-yl |
| 3.120 | OH | H | 3-methyl-4-chlorisoxazol-5-yl |
| 3.121 | OH | H | 3-methylisoxazol-4-yl |
| 3.122 | OH | H | isoxazol-4-yl |
| 3.123 | OH | H | 3,5-dimethylisoxazol-4-yl |
| 3.124 | OH | H | 2-methyloxazol-4-yl |
| 3.125 | OH | H | oxazol-2-yl |
| 3.126 | OH | H | 2-methylthiazol-4-yl |
| 3.127 | OH | H | 2-phenylthiazol-4-yl |
| 3.128 | OH | H | thiazol-4-yl |
| 3.129 | OH | H | 2-benzylthiazol-4-yl |
| 3.130 | OH | H | 5-chloro-2-phenylthiazol-4-yl |
| 3.131 | OH | H | thiazol-2-yl |
| 3.132 | OH | H | thiazol-5-yl |
| 3.133 | OH | H | 4-methylthiazol-2-yl |
| 3.134 | OH | H | 5-methylthiazol-2-yl |
| 3.135 | OH | H | 4-phenylthiazol-2-yl |
| 3.136 | OH | H | 4-methylthiazol-5-yl |
| 3.137 | OH | H | 2-methylthiazol-5-yl |
| 3.138 | OH | H | 2-phenylthiazol-5-yl |
| 3.139 | OH | H | [1,3,4]-thiadiazol-2-yl |
| 3.140 | OH | H | 5-methyl-[1,3,4]-thiadiazol-2-yl |
| 3.141 | OH | H | 5-phenyl-[1,3,4]-thiadiazol-2-yl |
| 3.142 | OH | H | 2-pyridyl |
| 3.143 | OH | H | 4-pyridyl |
| 3.144 | OH | H | 6-methyl-2-pyridyl |
| 3.145 | OH | H | 3-chloro-5-pyridyl |
| 3.146 | OH | H | 5-chloro-2-pyridyl |
| 3.147 | OH | H | quinolin-2-yl |
| 3.148 | OH | H | quinolin-4-yl |
| 3.149 | OH | H | quinolin-8-yl |
| 3.150 | OH | H | 7-chloroquinolin-8-yl |
| 3.151 | OH | H | 7-chloro-3-methylquinolin-8-yl |
| 3.152 | OH | H | 3,7-dichloroquinolin-8-yl |
| 3.153 | OH | H | 1-naphthyl |

TABLE 3-continued
Salicylic acid derivatives of the formula II'

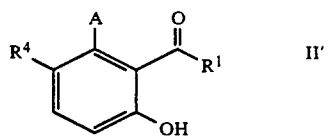

| No. | R¹ | R⁴ | A | |
|---|---|---|---|---|
| 3.154 | OH | H | 2-naphthyl | 159–176 |
| 3.155 | OH | H | 2-methyl-1-naphthyl | |
| 3.156 | OH | H | 2-methoxy-1-naphthyl | |
| 3.157 | OH | H | 1-chloro-4-naphthyltriazol-5-yl | |
| 3.158 | OCH₃ | H | 1,4-dichlorophenyl | 120–147/0.53 |
| 3.159 | OCH₃ | H | 3,5-dichlorophenyl | 145–160/0.27 |
| 3.160 | OCH₃ | H | pyrazol-1-yl | oil |
| 3.161 | OCH₃ | H | 4-fluorophenyl | 114–135/0.27 |
| 3.162 | OCH₃ | H | 4-methylphenyl | 140–147/0.8 |
| 3.163 | OCH₃ | H | 4-methoxyphenyl | 156–185/0.57 |
| 3.164 | OCH₃ | H | 4-nitrophenyl | 107–120 |
| 3.165 | OCH₃ | H | 2-methoxyphenyl | 153–173/0.57 |
| 3.166 | OH | H | 4-nitrophenyl | >300ᵃ⁾ |
| 3.167 | OCH₃ | H | 4-tert.-butylphenyl | 158–178/0.66 |
| 3.168 | OCH₃ | H | 4-phenylphenyl | 195–220/0.57 |
| 3.169 | OCH₃ | H | 4-cyanophenyl | 182–215/1.33 |
| 3.170 | OH | H | 4-carboxyphenyl | 210–218 (decomp.) |
| 3.171 | OCH₃ | H | 4-phenoxyphenyl | 203–218/0.4 |
| 3.172 | OH | H | 4-phenoxyphenyl | 142–148 |
| 3.173 | OCH₃ | H | 4-(4'-fluorophenoxy)-phenyl | 203–220/0.57 |
| 3.174 | OH | H | 4-(4'-fluorophenoxy)-phenyl | 130–135 |
| 3.175 | OH | H | 4-phenylphenyl | 175–185 |
| 3.176 | OCH₃ | H | 2-naphthyl | 175–195/0.57 |
| 3.177 | OH | H | 2-nitrophenyl | 132–135 |
| 3.178 | OCH₃ | H | 4-bromophenyl | 156–173/1.33 |
| 3.179 | OCH₃ | H | 2-chlorophenyl | 126–151/0.4 |
| 3.180 | OCH₃ | CH₃ | phenyl | 147–172/0.8 |
| 3.181 | OCH₃ | H | 2-methylphenyl | 119–132/0.57 |
| 3.182 | OCH₃ | H | 3-pyridyl | 175–192/0.66 |
| 3.183 | OCH₃ | H | 2-thienyl | 118–160/0.4 |
| 3.184 | OCH₃ | H | 3-methylphenyl | 70–145/0.66 |
| 3.185 | OCH₃ | H | 4-chlorophenyl | 120–150/0.66 |
| 3.186 | OCH₃ | H | 2-fluorophenyl | 80–95/0.57 |
| 3.187 | OCH₃ | H | 3-methoxyphenyl | 160–175/0.66 |
| 3.188 | OH | H | 3-methoxyphenyl | |
| 3.189 | OCH₃ | H | 4-trifluoromethylphenyl | 120–160/0.66 |
| 3.190 | OH | H | 4-trifluoromethylphenyl | 120–160/0.66 |
| 3.191 | OC₂H₅ | H | phenyl | 150–162/1.33 |
| 3.192 | OH | H | 3-isopropyl-pyrazol-1-yl | 160–63 |
| 3.193 | OH | H | 3(5)-methylthio-1,2,4-triazol-1-yl | 215 (decomp.) |
| 3.194 | OH | H | 3(5)-methylthio-5(3)-methyl-1,2,4-triazol-1-yl | 130 (decomp.) |
| 3.195 | OH | H | 3(5)-phenyl-5(3)-methyl-1,2,4-triazol-1-yl | 240 (decomp.) |

ᵃ⁾figures for the corresponding dipotassium salt

EXAMPLES DEMONSTRATING HERBICIDAL ACTION

The herbicidal action of the salicylic acid derivatives of the formula I is demonstrated in greenhouse experiments.

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The plants were either sown and grown in the same vessels, or they were grown separately as seedlings and transplanted to the test vessels a few days before treatment. The application rate for postemergence treatment was 0.5 kg/ha.

The pots were set up in the greenhouse, heat-loving species at 20° to 35° C., and species from moderate climates at 10° to 25° C. and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants employed for the experiments were *Bromus inermis, Echinochloa crus-galli* and Ipomoea spp.

Compound 1.004, applied postemergence at a rate of 0.5 kg/ha, provided excellent control of unwanted plants.

We claim:

1. A compound of the formula I

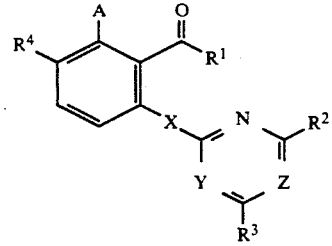

where
$R^1$ is hydrogen;
succinyliminooxy;
a 5-membered heteroaromatic radical selected from the group consisting of pyrrolyl, pyrazolyl, imidazolyl and triazolyl which may carry from one to four halogen atoms and/or one or two of the following radicals: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;
a radical $-OR^5$ or a radical $ON-CR^6R^7$, where
$R^5$ is hydrogen, an alkali metal cation, one equivalent of an alkaline earth metal cation or an organic ammonium ion;
$C_3$-$C_{12}$-cycloalkyl which may carry from one to three $C_1$-$C_4$-alkyl radicals;
$C_1$-$C_{10}$-alkyl which may carry from one to five halogen atoms and carries one of the following radicals: a 5-membered heteroaromatic radical selected from the group consisting of pyrrolyl, pyrazolyl, imidazolyl and triazolyl which may carry from one to four halogen atoms and/or one or two of the following radicals: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio; $C_2$-$C_6$-alkyl which carries one of the following radicals in the 2-position: $C_1$-$C_6$-alkoxyimino, $C_3$-$C_6$-alkenyloxyimino, $C_3$-$C_6$-haloalkenyloxyimino or benzyloxyimino, $C_3$-$C_6$-alkenyl or $C_3$-$C_6$-alkynyl, where these groups may in turn carry from one to five halogen atoms; phenyl which is unsubstituted or monosubstituted to trisubstituted by $C_1$-$C_4$-alkyl or by $C_1$-$C_4$-alkoxy or monosubstituted to pentasubstituted by halogen;
$R^6$ and $R^7$ are each $C_1$-$C_{20}$-alkyl which may carry phenyl, $C_1$-$C_4$-alkoxy and/or $C_1$-$C_4$-alkylthio, or are each phenyl or together form a $C_3$-$C_{12}$-alkylene chain which may carry from one to three $C_1$-$C_3$-alkyl groups;
$R^2$ and $R^3$ are each $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;
X is oxygen or sulfur;
Y and Z are each nitrogen;
$R^4$ is hydrogen, halogen, $C_1$-$C_4$-alkyl, cyano or $C_1$-$C_4$-haloalkyl;
A is an unsubstituted or monosubstituted to trisubstituted, or with halogen as substituent, monosubstituted to pentasubstituted phenyl radical

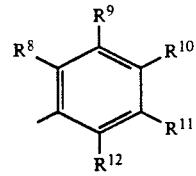

where $R^8$ ro $R^{12}$ are each hydrogen, halogen, cyano or nitro;
$C_3$-$C_6$-alkenyl, $C_3$-$C_6$-alkenyloxy, $C_3$-$C_6$-alkynyloxy or $C_3$-$C_6$-alkynyl, where these groups may in turn carry from one to five halogen atoms;
di-$C_1$-$C_4$-alkylamino or $C_3$-$C_8$-cycloalkyl which may carry from one to three $C_1$-$C_4$-alkyl radicals;
$C_1$-$C_{10}$-alkoxycarbonyl or $C_1$-$C_4$-alkylthio; phenoxy, where the aromatic radical may carry from one to five halogen atoms and/or from one to three of the following radicals: $C_1$-$C_4$-alkyl, $C_1$-$C_4$-haloalkyl; $C_1$-$C_4$-haloalkoxy, $C_1$-$C_4$-alkoxy or $C_1$-$C_4$-alkylthio; and $C_1$-$C_{10}$-alkyl or alkoxy which may carry from one to five halogen atoms and/or one of the following radicals: $C_1$-$C_4$-alkoxy, $C_1$-$C_4$-alkylthio, phenyl or phenoxy, where the aromatic radicals may in turn carry from one to five halogen atoms and/or from one to three of the following radicals: $C_1$-$C_4$-alkyl, $C_1$-$C_4$-haloalkyl, $C_1$-$C_4$-haloalkoxy or $C_1$-$C_4$-alkylthio;
or A is a 5-membered heteroaromatic radical selected from the group consisting of pyrazol-1-yl, 4-methylpyrazol-1-yl, 3,5-dimethylpyrazol-1-yl, 3,4,5-trimethylpyrazol-1-yl, 4-chloropyrazol-1-yl, 4-phenylpyrazol-1-yl, 4-isopropylpyrazol-1-yl, 4-nitropyrazol-1-yl, imidazol-1-yl, 4,5-dimethylimidazolyl, 2-methyl-4,5-dichloroimidazolyl, 4(5)-nitroimidazol-1-yl, [1,2,4]-triazol-1-yl, 3(5)-methyl-[1,2,4]-triazol-1-yl [1,2,3]-triazol-1-yl, 4,5-dimethyl-[1,2,3]-triazol-1-yl, [1,2,3,4]-tetrazol-1-yl, 1-methylpyrazol-4-yl, 1-phenylpyrazol-4-yl, 1,3,5-trimethylpyrazol-4-yl, 1-methylpyrazol-5-yl, 1-phenylpyrazol-5-yl, 1-methylpyrazol-3-yl, 1-phenylpyrazol-3-yl, 1-methylimidazol-2-yl, 1-methylimidazol-5-yl, 1-phenylimidazol-5-yl, 1-phenyl[1,2,3]-triazol-4-yl, isoxazol-5-yl, isoxazol-4-yl, 3-methylisoxazol-5-yl, 3-isopropyl-isoxazol-5-yl, 3-phenylisoxazol-5-yl, oxazol-2-yl, 2-methyloxazol-4-yl, thiazol-4-yl, 2-benzthiazol-4-yl, 4-methylthiazol-2-yl, 4-methylthiazol-5-yl, 4-phenylthiazol-2-yl and phenylthiazol-5-yl; thienyl which may carry from one to three halogen atoms and/or from one to three of the following radicals: $C_1$-$C_4$-alkyl, $C_1$- or $C_2$-haloalkyl or nitro; pyridyl which may carry from one to three halogen atoms and/or from one to three of the following radicals: $C_1$-$C_4$-alkyl, $C_1$- or $C_2$-haloalkyl or nitro; a naphthyl, quinolyl, indazolyl or benzotriazolyl radical, each of which may carry from one to three halogen atoms and/or from one to three of the following radicals:
$C_1$-$C_4$-alkyl or $C_1$- or $C_2$-haloalkyl,
and environmentally compatible salts of the compounds I.

2. A herbicidal composition containing a herbicidally effective amount of a compound of formula I as defined in claim 1 along with conventional carriers and/or diluents.

3. A process for combating the growth of unwanted plants, wherein the unwanted plants and/or their habitat are treated with a herbicidally effective amount of a derivative I as defined in claim 1.

4. A composition for influencing plant growth which comprises a growth regulating amount of a salicylaldehyde derivative or a salicylic acid derivative of the formula I as defined in claim 1 along with conventional carriers and/or diluents.

5. A process for influencing plant growth, wherein a bioregulatory effective amount of a salicylaldehyde derivative or a salicylic acid derivative of the formula I as defined in claim 1 is allowed to act on the seeds, plants and/or their habitat.

6. A compound of the formula I as defined in claim 1, wherein $R^1$ is OH, $R^2$ is methoxy, $R^3$ is methoxy, $R^4$ is hydrogen and A is 4-trifluoromethylphenyl.

7. A compound of the formula I as defined in claim 1, wherein $R^1$ is OH, $R^2$ is methoxy, $R^3$ is methoxy, $R^4$ is hydrogen and A is phenyl.

8. A compound of the formula I as defined in claim 1, wherein $R^1$ is $OR^5$ and $R^5$ is H, an alkali metal cation, one equivalent of an alkaline earth metal cation or an organic ammonium ion.

9. A compound of the formula I as defined in claim 1, wherein $R^1$ is OH.

10. A compound of the formula I as defined in claim 1, wherein $R^1$ is OH and $R^4$ is H.

11. A process for combatting the growth of unwanted plants which comprises: applying to the unwanted plants and/or their habitat a herbicidally effective amount of a compound as defined in claim 6.

12. A process for combatting the growth of unwanted plants which comprises: applying to the unwanted plants and/or their habitat a herbicidally effective amount of a compound as defined in claim 7.

13. A process for combatting the growth of unwanted plants which comprises: applying to the unwanted plants and/or their habitat a herbicidally effective amount of a compound as defined in claim 8.

14. A process for combatting the growth of unwanted plants which comprises: applying to the unwanted plants and/or their habitat a herbicidally effective amount of a compound as defined in claim 9.

15. A process for combatting the growth of unwanted plants which comprises: applying to the unwanted plants and/or their habitat a herbicidally effeceive amount of a compound as defined in claim 10.

* * * * *